US007173011B2

(12) United States Patent
Rodgers et al.

(10) Patent No.: US 7,173,011 B2
(45) Date of Patent: *Feb. 6, 2007

(54) RADIATION THERAPY METHODS

(75) Inventors: Kathleen E. Rodgers, Long Beach, CA (US); Gere DiZerega, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 347 days.

This patent is subject to a terminal disclaimer.

(21) Appl. No.: 10/341,001

(22) Filed: Jan. 13, 2003

(65) Prior Publication Data

US 2003/0130196 A1 Jul. 10, 2003

(51) Int. Cl.
*A61K 38/08* (2006.01)
*C07K 7/00* (2006.01)
*C07K 7/14* (2006.01)
*C07K 5/103* (2006.01)
*C07K 5/113* (2006.01)

(52) U.S. Cl. .......................... 514/16; 514/17; 530/328; 530/329

(58) Field of Classification Search .................... 514/2, 514/16
See application file for complete search history.

(56) References Cited

U.S. PATENT DOCUMENTS

| | | | |
|---|---|---|---|
| 5,015,629 A | 5/1991 | DiZerega | |
| 5,155,211 A | 10/1992 | Rosenberg | |
| 5,178,856 A | 1/1993 | Burstein | |
| 5,186,931 A | 2/1993 | Kishimoto et al. | |
| 5,486,359 A | 1/1996 | Caplan et al. | |
| 5,599,712 A | 2/1997 | Greenberger et al. | |
| 5,616,561 A | 4/1997 | Barcellos-Hoff | |
| 5,629,292 A | 5/1997 | Rodgers et al. | |
| 5,693,616 A | 12/1997 | Krstenansky et al. | |
| 5,716,935 A | 2/1998 | Rodgers et al. | |
| 5,955,430 A | 9/1999 | Rodgers et al. | |
| 6,239,109 B1 * | 5/2001 | Rodgers et al. | 514/16 |
| 6,248,587 B1 | 6/2001 | Rodgers et al. | |
| 6,335,195 B1 * | 1/2002 | Rodgers et al. | 435/377 |
| 6,455,500 B1 * | 9/2002 | Rodgers et al. | 514/16 |
| 6,475,988 B1 | 11/2002 | Rodgers et al. | |
| 6,566,335 B1 * | 5/2003 | Rodgers et al. | 514/15 |
| 6,747,008 B1 | 6/2004 | Rodgers et al. | |
| 6,821,953 B1 | 11/2004 | Rodgers et al. | |

FOREIGN PATENT DOCUMENTS

| EP | 0 265 400 | 8/1987 |
|---|---|---|
| WO | WO 95/08337 | 3/1995 |
| WO | WO 95/08565 | 3/1995 |
| WO | WO 96/93164 | 12/1996 |
| WO | WO 97 34627 | 9/1997 |

OTHER PUBLICATIONS

T. Kato, et al., "New Modality of Radiation Therapy Under Increased Tumor Oxygen Tension with Angiotensin II: A Pilot Study," Radiation Medicine, vol. 11, No. 3, 1993, pp. 86-90.
Katrina Bedecs, Nathalie Elbaz, Malene Sutren, Maryline Mason, Christiane Susin, A. Donny Strosberg, Clara Nahmias, "Angiotensin II Type 2 Receptors Mediate Inhibition of Mitogen-Activated Protein Kinase Cascade and Functional Activation of SHP-1 Tyrosine Phosphatase," Biochem. J., vol. 325, (1997) pp. 449-454.
Leonard Bell and Joseph A. Madri, "Influence of the Angiotensin System on Endothelial and Smooth Muscle Cell Migration," American Journal of Pathology, vol. 137, No. 1, (1990) pp. 7-12.
Bradford C. Berk, Vladimir Vekshtein, Helen M. Gordon, Terutaka Tsuda, "Angiotensin II-Simulated Protein Synthesis in Cultured Vascular Smooth Muscle Cells," Hypertension, vol. 13 (1989) pp. 305-314.
Arthur E. Bogden, Patrice Carde, Evelyne Deschamps de Paillette, Jacques-Pierre Moreau, Maurice Tubiana and Emilia Frindel, "Amelioration of Chemotherapy-Induced Toxicity by Co-treatment with AcSDKP, A Tetrapeptide Inhibitor of Hematopoietic Stem Cell Proliferation," Annual N.Y. Acad. Sci. vol. 628 (1991) pp. 126-139.
Susan E. Bryson, Philip Warburton, Helen P. Wintersgill, G. Michael Drew, Anton D. Michel, Stephen G. Ball and Anthony J. Balmforth, "Induction of the Angiotensin $AT_2$ Receptor Subtype Expression by Differentiation of the Neuroblastoma x Glioma Hybrid, NG-108-15," European Journal of Pharmacology, vol. 225 (1992) 119-127.
Rose-Marie Catalioto, Anna-Rita Renzetti, Marco Criscuoli, Jacques Mizrahi, Alessandro Subissi, "Angiotensins Induce the Release of Prostacyclin from Rabbit Vas Deferens: Evidence for Receptor Heterogeneity," European Journal of Pharmacology, vol. 256 (1994) 93-97.
Eric P. Cohen, Angostino Molteni, Patricia Hill, Brian L. Fish, William F. Ward, John E. Moulder and Frank A. Carone, Captopril Preserves Function and Ultrastructure in Experimental Radiation Nephropathy, Laboratory Investigation, vol. 75, No. 3 (1996), pp. 349-360.
Eric p. Cohen, John E. Moulder, Brian L. Fish ad Patricia Hill, "Prophylaxis of Experimental Bone Marrow Transplant Nephropathy," J. Lab. Clin. Med., vol. 124 (1994) pp. 371-380.
Eric P. Cohen, Brian L. Fish and John E. Moulder, "Successful Brief Captopril Treatment in Experimental Radiation Nephropathy," J. Lab Clin. Med., vol. 129 (1997) pp. 536-547.

(Continued)

*Primary Examiner*—Michael Borin
(74) *Attorney, Agent, or Firm*—McDonnell Boehnen Hulbert & Berghoff LLP

(57) ABSTRACT

The present invention provides methods and kits for mitigating radiation induced tissue damage, improving the effectiveness of radiation therapy, to support bone marrow transplantation, and promoting megakaryocyte production and mobilization and platelet production, each method comprising the administration of an effective amount of angiotensinogen, angiotensin I (AI), AI analogues, AI fragments and analogues thereof, angiotensin II (AII), AII analogues, AII fragments or analogues thereof or AII $AT_2$ type 2 receptor agonists.

15 Claims, 24 Drawing Sheets

OTHER PUBLICATIONS

H,J. Deeg, K. Seidel, D.S. Hong, C. Yu, R. Huss, F.G. Schuening, C.H. Ewel and R. Storb, "In Vivo Radioprotective Effect of AcSDKP on Canine Myelopoiesis," Ann. Hematology, vol. 74 (1997) pp. 117-122.

David J. Dunlop, Eric G. Wright, Sally Lorimore, Gerard J. Graham, Tessa Holyoake, David J. Kerr, Stephen D. Wolpe and Ian B. Pargness, "Demonstration of Stem Cell Inhibition Myeloprotective Effects of SCI/rhMIP1α In Vivo," Blood, vol. 79, No. 9 (1992) pp. 2221-2225.

Victor E. Dzau, Richard Pratt, Gary Gibbons, Heribert Schunkert, Beverly Lorell and Julie Ingelfinger, "Molecular Mechanism of Angiotensin in the Regulation of Vascular and Cardiac Growth," J. Mol. Cell. Cardiol., vol. 21 (Supplemental III) (1989) p. S.7.

Richard M. Edwards and Elwood J. Stack, "Angiotensin II Inhibitors Glomerular Adenylate Cyclase via the Angiotensin II Receptor Subtype 1 ($AT_1$)," The Journal of Pharmacology and Experimental Therapeutics, vol. 266, No. 2 (1993) pp. 506-510.

Leonardo A. Fernandez, Jeff Twickler and Alden Mead, "Neovascularization Produced by Angiotensin II," vol. 105, No. 2 (1985) pp. 141-145.

J. P. Geraci, M-C. Sun and M.S. Mariano, "Amelioration of Radiation Nephropathy in Rats by Post-Radiation Treatment with Dexamethasone and/or Captopril," Radiation Research, vol. 143 (1995) pp. 58-68.

Neelam Jaiswal, E. Ann Tallant, Debra I. Diz, Mahesh C. Khosla and Carlos M. Ferrario, "Subtype 2 Angiotensin Receptors Mediate Prostaglandin Synthesis in Human Astrocytes," Hypertension, vol. 17 (1991) pp. 1115-1120.

Neelam Jaiswal, E. Ann Tallant, Rama K. Jaiswal, Debra I. Diz and Carlos M. Ferrarion, "Differential Regulation of Prostaglandin Synthesis by Angiotensin Peptides in Porcine Aortic Smooth Muscle Cells: Subtypes of Angiotensin Receptors Involved," the Journal of Pharmacology and Experimental therapeutics, vol. 266, No. 2 (1991) pp. 664-673.

Neelam Jaiswal, Debra I. Diz, Mark C. Chappell, Mahesh C. Khosla and Carlos M. Ferrario, "Stimulation of Endothelial Cell Prostaglandin Production by Angiotensin Peptides," Hypertension, (Supplemental II) (1992) II-49-II-55).

Philip Janiak, Aline Pilon, Jean-Francois Prost and jean-Paul Vilaine, "Role of Angiotensin Subtype 2 Receptor in Neointima Formation After Vascular Injury," Hypertension, vol. 20 (1992) pp. 737-745.

Toshio Kato, Yuko Murakami, Yutaka Saito, Noriaki Tomura, Masaaki Shindo, Jiro Watarai and Yoshiharu Tamakawa, new Modality of Radiation Therapy Under Increased Tumor Oxygen Tension with Angiotensin II: A Pilot Study, Radiation medicine, vol. 11, No. 3 (1993) pp. 86-91.

Raymond F. Kauffman, James S. Bean, Karen M. Zimmerman, Raymond F. Brown, and Mitchell I. Steinberg, "Losartan, A Nonpeptide Angiotensin II (ANG II) Receptor Antagonist, Inhibits Neointima Formation Following Balloon Injury To Rat Cartoid Arteries," Life Sciences, vol. 49, (1991) pp. 223-228.

Yasuhiro Kawahara, Michitoshi Sunako, Terutaka Tsuda, Hisashi Fukuzaki, Yasuo Fukumoto and Yoshimi Takai, "Angiotensin II Induces Expression of the C-fos Gene Through Protein Kinase C. Activation and Calcium Ion Mobilization in Cultured Vascular Smooth Muscle Cells," Biochemical and Biophysical Research Communication, vol. 150, No. 1 (1988) pp. 52-59.

Birgitta Kimura, Colin Sumners and M. Ian Philllips, "Changes in Skin Angiotensin II Receptors in Rats During Wound Healing," Biochemical and Biophysical Research Communication, vol. 187, No. 2 (1992) pp. 1083-1090.

Ferdinand A.C. Le Noble, Johan W.M. Hekking, Henny W. M. Van Straaten, Dick W. Slaff, and Harry A.J. Struyker Boudier, "Angiotensin II Stimulates Angiotensins in the Chorio-Allantoic Membrane of the Chick Embryo," European Journal of Pharmacology, vol. 195 (1991) pp. 305-306.

A. Masse, L.H. Ramirez, G. Bindoula, C. Grillon, J. Wdzieczak-Bakala, K. Raddassi, E. Deschamps de Paillette, J.M. Mencia-Huerta, S. Koscielny, P. Potier, F. Sainteny and P. Carde, "The Tetrapeptide Acetyl-N-Ser-Lys-Pro (Goralatide) Protects from Doxorubicin-Induced Toxity: Improvement in Mice Survival and protection of Bone Marrow Stem Cells and Progenitors," Blood, vol. 91 91998) pp. 441-449.

Simone Meffert, Monika Stoll, Ulrike M. Stecklings, Serge P. Bottari, Thomas Unger, "The Angiotensin II $AT_2$ Receptor Inhibits Proliferation and Promotes Differentiation in PC12W Cells," Molecular and Cellular Endicronology, vol. 122 (1996) pp. 59-67.

John E. Moulder, Eric P. Cohen, Brian L. Fish and Patricia Hill, "Prophylaxis of Bon Marrow Transplant Nephropathy with Captopril, an Inhibitor of Angiotensin-Converting Enzyme," Radiation Research, vol. 136 (1993) pp. 404-407.

John E. Moulder, Brian L. Fish, Eric P. Cohen and Stephen M. Bonsib, Angiotensin Ii Receptor Antagonist in the Prevention of Radiation Nephropathy, Radiation Research, vol. 146 (1996) pp. 106-110.

John E. Moulder, Brian L. Fish and Eric P. Cohen, "Treatment of Radiation Nephropathy with Ace Inhibitors," Int. J. Radiation Oncology Bio. Phys., vol. 27 (1993) pp. 93-99.

J.E. Moulder, B.L. Fish, and E.P. Cohen, "Noncontinuous use of Angiotensin Converting Anzyme Inhibitors in the Treatment of Experimental Bone Marrow Transplant Nephropathy," Bone Maroow Transplantation, vol. 19 (1997) pp. 729-735.

Allen J. Naftilan, Richard E. Pratt, and Victor J. Dzau, "Induction of Platelet-Derived Growth Factor A-Chain and c-myc Gene Expression by Angiotensin II in Cultured Rat Vascular Smooth Muscle Cells," J. Clin. Invest., vol. 83 (1989) pp. 1419-1423.

Ken-Ichi nakahara, Hiroshi Nishimura, Makoto Kuro-o, Shun-Ichi Takewaki, Misaki Iwase, Akiyuki Ohkubo, Yoshio Yazaki, and Ryozo Nagai, "Identification of Three Types of PDGF-A Chain Gene Transcripts in Rabbit Vascular Smooth Muscle and Their Regulated Expression During Development and by Angiotensin II," Biochemical and biophysical Research Communications, vol. 184, No. 2 (1992) pp. 811-818.

Walter R. Paukovits, Marie-Helene Moser and Johanna B. Paukovits, "Pre-CFU-S Quiescence and Stem Cell Exhaustion After Cytostatic Drug Treatment: Protective Effects of the Inhibitory Peptide pGlu-Glu-Asp-Cys-Lys (pEEDCK)," Blood, vol. 81, No. 7 (1993) pp. 1755-1761.

Josef Pfeilschifter, Andrea Huwiler, Claire Merriweather and Vreny A. Briner, "Angiotensin II Stimulation of Phospholipase D in rat Renal Mesangial Cells is Mediated by the $AT_1$ Receptor Subtype," European Journal of Pharmacology, vol. 225 (1992) pp. 57-62.

Ilkka Portsi, Agnieszka T. Bara, Rudi Busse and Markus Hecker, "Release of Nitric Oxide by Angiotensin-(1-7) from Porcine Coronary Endothelium: Implications for a Novel Angiotensin Receptor," Br. J. Pharmacol., vol. 111 (1994) pp. 652-654.

Margaret Forney-Prescott, Randy L. Webb and Michael A. Reidy, "Angiotensin-Converting Enzyme Inhibitor Versus Angiotensin II, $AT_1$ Receptor Antagonist," Am. J. Pathol. vol. 139 (1991) pp. 1291-1296.

D. Regoli, W. K. park and F. Rioux, "Pharmacology of Angiotensin," Pharmacological Reviews, vol. 25, No. 2 (1974) pp.69-123.

Robert C. Speth and Kwan Hee Kim, "Discrimination of Two Angiotensin II Receptor Subtypes with a Selective Agonist Analogue of Angiotensin II, p-Aminophenylalanine Angiotensin II," vol. 169, No. 3 (1990) pp. 997-1006.

George A. Stouffer and Gary K. Owens, "Angiotensin II-Induces Mitogenesis of Spontaneously Hypertensive Rat-Derived Cultured Smooth Cells is Dependent on Autocrine Production of Transforming Growth Factor-β," Circulation Research, vol. 70 (1992) pp. 820-828.

Mark B. Taubman, Bradford C. Berk, Seigo Izumo, Terutaka Tsuda, R. Wayne Alexander and Bernardo Nadal-Ginard, "Angiotensin II Induces c-fos mRNA in Aortic Smooth Muscle," The Journal of Biological Chemistry, vol. 264, No. 1 (1989) pp. 526-530.

Mohan Viswanathan and Juan M. Saaverdra, "Expression of Angiotensin II $AT_2$ Receptors in the Rat Skin During Experimental Wound Healing," peptides, vol. 13 (1992) pp. 783-786.

William F. Ward, Pei-Jan Paul Lin, Ping S. Wong, Rahim Behnia and Nassar Jalali, "Radiation Pneumonitis in Rats and Its Modification by the Angiotensin-Converting Enzyme Inhibitor Captopril Evaluated by High-Resolution Computed Tomography," Radiation Research, vol. 135, (1993) pp. 81-87.

Tsutomu Watanabe, Linda S. Kelsey, Yun Yan, Gregory S. Brown, John D. Jackson, Cynthia Ewel and Henri Beaufour, "In Vivo Haemoprotective Activity of Tetrapeptide AcSDKP Combined with Granulocyte-Colony Stimulating Factor Following Sublethal Irradiation," British Journal of Hematology, vol. 96 (1996) pp. 619-627.

Gunter Wolf, Uwe Haberstroh and Eric G. Neilson, "Angiotensin II Stimulates the Proliferation and Biosynthesis of Type I Collagen in Cultured Murine Mesangial Cells," American Journal of Pathology, vol. 40, No. 1 (1992) pp. 95-107.

Sei-Chul Yoon, Jeong-Mi Park, Hong-Seok Lang, Kyung-Sub Shinn and Yong-Whee Bahk, "Radioprotective Effect of Captopril on the Mouse Jejunal Mucosa," Int. J. Radiation Oncology Bio. Phys., vol. 30, No. 4 (1994) pp. 873-878.

* cited by examiner

RADIATION THERAPY METHODS

CROSS REFERENCE

This application is a Continuation-In-Part of U.S. Provisional Application Nos. 60/077,382 filed Mar. 10, 1998; Ser. No. 60/083670 filed Apr. 29, 1998; Ser. No. 60/081,262 filed Apr. 9, 1998; Ser. No. 60/090216 filed Jun. 22, 1998; Ser. No. 60/090,096 filed Jun. 19, 1998; and 60/099,957 filed Sep. 11, 1998.

BACKGROUND OF THE INVENTION

Radiation therapy is currently one of the most useful methods of treating cancerous tumors. However, radiation therapy damages normal tissue surrounding the tumor (U.S. Pat. No. 5,599,712, incorporated by reference herein in its entirety). This damage can include fibrosis, remodeling of the extracellular matrix, vascular damage, aberrant angiogenesis, pneumonitis, atherogenesis, osteonecrosis, mucositis, immunosuppression and functional impairment (U.S. Pat. No. 5,616,561, incorporated by reference herein in its entirety). As a result of these radiation-induced side effects, techniques have been developed to minimize radiation-induced damage to surrounding normal tissues by limiting radiation to the lowest level effective for cancer treatment. Since there is a direct relationship between the amount of radiation and the effectiveness of the treatment, this method compromises the overall effectiveness of the treatment.

For some cancer patients, hematopoietic toxicity frequently limits the opportunity for radiation dose escalation (Watanabe et al., British J. Haematol. 94:619–627 (1996)). Repeated or high dose cycles of radiation therapy may be responsible for severe stem cell depletion leading to important long-term hematopoietic sequelea and marrow exhaustion (Masse et al., Blood 91:441–449 (1998). Such stem cell depletion leads to depletion of the full range of hematopoietic lineage specific cells, including megakaryocytes, platelets, monocytes, neutrophils, and lymphocytes, and the resulting complications of such depletion. For example, in patients suffering from depressed levels of platelets (thrombocytopenia) the inability to form clots is the most immediate and serious consequence, a potentially fatal complication of many therapies for cancer. Such cancer patients are generally treated for this problem with platelet transfusions. Other patients frequently requiring platelet transfusions are those undergoing bone marrow transplantation or patients with aplastic anemia. Platelets for such procedures are obtained by plateletpheresis from normal donors. Like most human blood products, platelets for transfusion have a relatively short shelf-life and also expose the patients to considerable risk of exposure to dangerous viruses, such as the human immunodeficiency virus (HIV).

The administration of hematopoietic growth factors may reduce short-term side effects induced by radiation, but has been hypothesized to cause long-term hematopoietic damage (Masse et al., 1998; Watanabe et al., 1996). Several studies have suggested that co-administration of negative hematopoietic regulators can minimize radiation therapy-induced myelotoxicity by reducing the number of progenitor cells that enter the cell cycle. (Watanabe et al., 1996; Dunlop et al., Blood 79:2221–2225 (1992); Paukovits et al., Blood 81: 1755–1761; Bogden et al., Annals N.Y. Acad. Sci. 628:126–139 (1991); Deeg et al., Ann. Hematol. 74:117–122 (1997); Masse et al., 1998). This treatment is based on the premise that hematopoietic stem cells are relatively protected from radiation-related toxicity when quiescent, particularly when the malignant cells are proliferating (Deeg et al., (1997)).

Bone marrow contains pluripotent stem cells that are capable of reconstituting the entire hematopoietic system. Bone marrow transplantation has been used to treat various intractable hematopoietic diseases including leukemia and severe aplastic anemia. (U.S. Pat. No. 5,186,931, incorporated by reference herein in its entirety.) Typically, a bone marrow transplant patient is subjected to irradiation to reduce the leukocyte count to zero, followed by transplantation of bone marrow cells which function by producing a sufficient number of normal leukocytes. However, various complications, such as death, infectious diseases, graft versus host disease, radiation nephritis, and interstitial pneumonia frequently occur during the time period between transplantation and the return to normal white blood cell levels after transplantation.

As a result of these frequent side effects, no satisfactory methods are currently available for supporting bone marrow transplantation which are capable of both increasing survival of bone marrow transplant patients and also accelerating the reconstitution of the hematopoietic system of the patient.

Chronic radiation injuries, such as radiation nephropathy, have been viewed as inevitable, progressive and untreatable (Moulder et al., Bone Marrow Transplantation 19:729–735 (1997)). The progressive and untreatable nature of late tissue damage follows from the assumption that the injury is due to delayed mitotic cell death resulting from genetic injury that is produced and irrevocably fixed in place at the time of irradiation (Moulder et al., 1997). Under this view, the only way to decrease the probability of injury is by limiting the radiation dose or shielding the at risk organs.

However, recent results indicate that late-onset radiation-induced tissue injury involves complex and dynamic interactions among parenchymal and vascular cells within a particular organ (Moulder et al., 1997). This model of chronic radiation injury suggests that pharmacological intervention after radiation exposure would be effective.

Thus, despite advances in the field of radiation therapy, prior art methods have proven to be of limited utility in minimizing radiation-induced tissue damage, and improving the efficacy of tumor radiation therapy and bone marrow transplantation. Thus, there is a need for improved therapeutic methods to mitigate radiation induced tissue damage and to improve the effectiveness of radiation therapy. Furthermore, the ability to stimulate endogenous platelet formation in thrombocytopenic patients with a concomitant reduction in their dependence on platelet transfusion would be of great benefit. In addition the ability to correct or prevent thrombocytopenia in patients undergoing radiation therapy or chemotherapy for cancer would make such treatments safer and possibly permit increases in the intensity of the therapy thereby yielding greater anti-cancer effects.

SUMMARY OF THE INVENTION

In one aspect, the present invention provides methods and kits for mitigating radiation induced tissue damage, improving the effectiveness of radiation therapy, to support bone marrow transplantation, and promoting megakaryocyte production and mobilization and platelet production, each method comprising the administration of angiotensinogen, angiotensin I (AI), AI analogues, AI fragments and analogues thereof, angiotensin II (AII), AII analogues, AII fragments or analogues thereof or AII $AT_2$ type 2 receptor agonists to a patient in need thereof.

In another aspect of the present invention, an improved cell culture medium and kits are provided for the production of megakaryocytes and platelets wherein the improvement comprises addition to the cell culture medium of an effective amount of angiotensinogen, AI, AI analogues, AI fragments and analogues thereof, AII, AII analogues, AII fragments or analogues thereof or AII $AT_2$ type 2 receptor agonists.

These aspects and other aspects of the invention become apparent in light of the following detailed description.

DETAILED DESCRIPTION OF THE PREFERRED EMBODIMENTS

Figure 1:
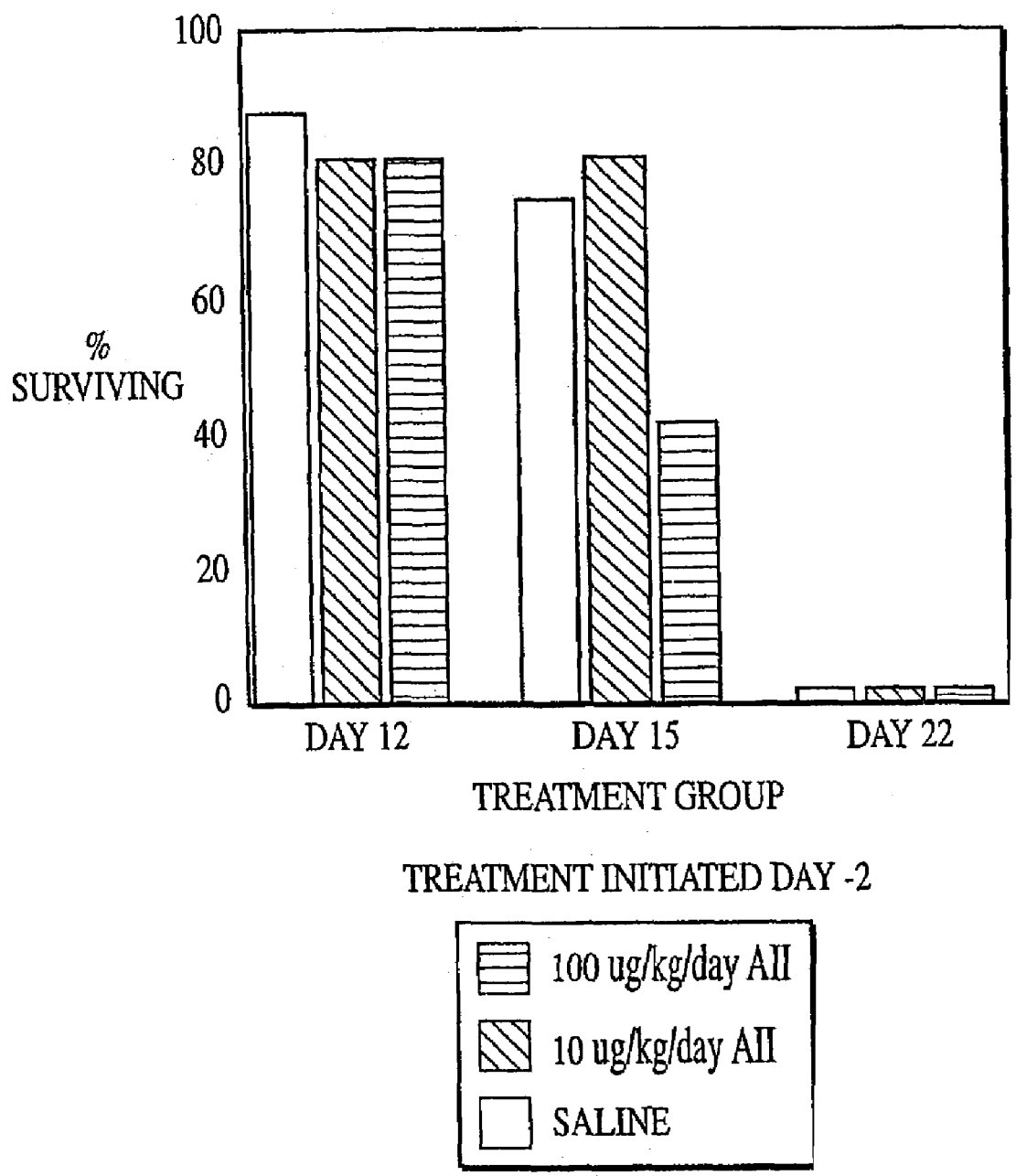
FIG. 1 is a graph showing the effect of AII treatment two days prior to exposure on post-irradiation mouse mortality.

All references patents and patent applications are hereby incorporated by reference in their entirety.

The present invention fulfills the needs for improved therapeutic methods to mitigate radiation induced tissue damage, to improve the effectiveness of radiation therapy, to support bone marrow transplantation, and to promote megakaryocyte production and mobilization and platelet production.

As defined herein the phrase "mitigation of tissue damage" refers not only to reduction of damage, but also encompasses recovery of tissue from damage. As used herein "tissue" refers to any tissue type, and also includes hematopoietic stem and progenitor cells, white blood cells and platelets.

As defined herein the term "megakaryocyte mobilization" refers to the movement of a megakaryocyte precursor cell from the bone marrow into the periphery.

As defined herein, the phrase "improved platelet production" or "improved megakaryocyte production," means that the number of platelets or megakaryocytes is significantly elevated above the normal range of platelets or megakaryocytes in the particular mammal involved. The elevation of platelet or megakaryocyte counts may occur in a time-dependent manner, and may be cyclical, increasing and then constant or decreasing, or constant, etc.

Unless otherwise indicated, the term "active agents" as used herein refers to the group of compounds comprising angiotensinogen, angiotensin I (AI), AI analogues, AI fragments and analogues thereof, angiotensin II (AII), AII analogues, AI fragments or analogues thereof and AII $AT_2$ type 2 receptor agonists.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991, Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro-Phe [SEQ ID NO:1]. The biological formation of angiotensin is initiated by the action of renin on the plasma substrate angiotensinogen. The substance so formed is a decapeptide called angiotensin I (AI) which is converted to AII by the converting enzyme angiotensinase which removes the C-terminal His-Leu residues from AI (Asp-Arg-Val-Tyr-Ile-His-Pro-Phe-His-Leu [SEQ ID NO:37]). AII is a known pressor agent and is commercially available. The use of AII analogues and fragments, AT2 agonists, as well as AIII and AIII analogues and fragments in wound healing has also been described. (U.S. Pat. No. 5,629,292; U.S. Pat. No. 5,716,935; WO 96/39164; all references herein incorporated by reference in their entirety.)

Studies have shown that AII increases mitogenesis and chemotaxis in cultured cells that are involved in wound repair, and also increases their release of growth factors and extracellular matrices (diZerega, U.S. Pat. No. 5,015,629; Dzau et. al., *J. Mol. Cell. Cardiol.* 21:S7 (Supp III) 1989; Berk et. al., *Hypertension* 13:305–14 (1989); Kawahara, et al., *BBRC* 150:52–9 (1988); Naftilan, et al., *J. Clin. Invest.* 83:1419–23 (1989); Taubman et al., *J. Biol. Chem.* 264: 526–530 (1989); Nakahara, et al., *BBRC* 184:811–8 (1992); Stouffer and Owens, *Circ. Res.* 70:820 (1992); Wolf, et al., *Am. J. Pathol.* 140:95–107 (1992); Bell and Madri, *Am. J. Pathol.* 137:7–12 (1990). In addition, AII was shown to be angiogenic in rabbit corneal eye and chick chorioallantoic membrane models (Fernandez, et al., *J. Lab. Clin. Med.* 105:141 (1985); LeNoble, et al., *Eur. J. Pharmacol.* 195: 305–6 (1991). Therefore, AII may accelerate wound repair through increased neovascularization, growth factor release, reepithelialization and/or production of extracellular matrix.

AII has also been implicated in both cell growth and differentiation (Meffert et al., *Mol. and Cellul. Endocrin.* 122:59 (1996)). Two main classes of AII receptors, $AT_1$ and $AT_2$ have been identified (Meffert, 1996). The growth-promoting effects of AII have been attributed to mediation by the AT1 receptor, while some evidence suggests that the AT2 receptor may be involved in mediation of the cell differentiation effects of AII (Bedecs et al., *Biochem. J.* 325:449 (1997)).

The effects of AII receptor and AII receptor antagonists have been examined in two experimental models of vascular injury and repair which suggest that both AII receptor subtypes (AT1 and AT2) play a role in wound healing (Janiak et al., *Hypertension* 20:737–45 (1992); Prescott, et al., *Am. J. Pathol.* 139:1291–1296 (1991); Kauffman, et al., *Life Sci.* 49:223–228 (1991); Viswanathan, et al., *Peptides* 13:783–786 (1992); Kimura, et al., *BBRC* 187:1083–1090 (1992).

Many studies have focused upon AII(1–7) (AII residues 1–7) or other fragments of AII to evaluate their activity. AII(1–7) elicits some, but not the full range of effects elicited by AII. Pfeilschifter, et al., *Eur. J. Pharmacol.* 225:57–62 (1992); Jaiswal, et al., *Hypertension* 19(Supp. II):II-49–II-55 (1992); Edwards and Stack, *J. Pharmacol. Exper. Ther.* 266:506–510 (1993); Jaiswal, et al., *J. Pharmacol. Exper. Ther.* 265:664–673 (1991); Jaiswal, et al., *Hypertension* 17:1115–1120 (1991); Portsi, et a., *Br. J. Pharmacol.* 111:652–654 (1994).

While a single pilot study has suggested that AII-induced hypertension might be effective in combination with radiation therapy in the treatment of lung cancer patients (Kato et al., *Radiation Medicine* 11:86–90 (1993)), many studies have demonstrated that antagonists of angiotensin converting enzyme (ACE), which mediate the production of AII, are effective in reducing radiation nephropathy, bone marrow transplantation nephropathy, and acute radiation injury (Moulder et al., *Int. J. Radiation Onc. Biol. Phys.* 27:93–99 (1993); Moulder et al., *Bone Marrow Transpl.* 19:729–735 (1997); Moulder et al., *Radiation Res.* 146:106–110 (1996); Cohen et al., *J. Lab. Clin. Med.* 129:536–547 (1997); Moulder et al., *Radiation Res.* 136:404–407 (1993); Yoon et al., *Int. J. Radiat. Oncol. Biol. Phys.* 30:873–878 (1994); Ward et al., *Radiation Res.* 135:81–87 (1993); Cohen et al., *Lab. Invest.* 75:349–360 (1996); Cohen et al., *J. Lab. Clin. Med.* 124:371–380 (1994); Gerarci et al., *Radiation Res.* 143:58–68 (1995)). The effect of the ACE inhibitors has been demonstrated, in at least one case, to be directly caused by the reduction of activation of the AT1 receptor by AII (Moulder et al., *Radiation Res.* 146:106–110 (1996)). These results have led to the suggestion that, in the case of radiation nephropathy, the most effective treatment is the use of ACE inhibitors (Moulder et al., *Bone Marrow Transplantation* 19:729–735 (1997)).

Furthermore, it has recently been demonstrated that angiotensinogen, angiotensin I (AI), AI analogues, AI fragments and analogues thereof, AII, AII analogues, AII fragments or analogues thereof or AII $AT_2$ type 2 receptor agonists are potent stimulators of hematopoietic stem cell proliferation (U.S. patent application, Ser. No. 09/012,400, hereby incorporated by reference in its entirety). Therefore, it would be expected that the use of these compounds might cause long-term hematopoietic damage if used in conjunction with radiation therapy (Masse et al., 1998; Watanabe et al., 1996).

Based on all of the above, it would be unexpected that the use of angiotensinogen, angiotensin I (AI), AI analogues, AI fragments and analogues thereof, AII, AII analogues, AII fragments or analogues thereof or AII $AT_2$ type 2 receptor agonists would be effective in reducing radiation-induced human tissue damage or in treating patients in need of radiation therapy.

None of these studies teach or suggest the use of angiotensinogen, angiotensin I (AI), AI analogues, AI fragments and analogues thereof, angiotensin II (AII), AII analogues, AII fragments or analogues thereof or AII $AT_2$ type 2 receptor agonists to stimulate the production and mobilization of megakaryocytes, or to stimulate the production of platelets.

A peptide agonist selective for the AT2 receptor (AII has 100 times higher affinity for AT2 than AT1) is p-aminophenylalanine6-AII ["(p-$NH_2$-Phe)6-AII)"], Asp-Arg-Val-Tyr-Ile-Xaa-Pro-Phe [SEQ ID NO.36] wherein Xaa is p-$NH_2$-Phe (Speth and Kim, *BBRC* 169:997–1006 (1990). This peptide gave binding characteristics comparable to AT2 antagonists in the experimental models tested (Catalioto, et al., *Eur. J. Pharmacol.* 256:93–97 (1994); Bryson, et al., *Eur. J. Pharmacol.* 225:119–127 (1992).

The active AI, AI analogues, AI fragments and analogues thereof, AII analogues, fragments of AII and analogues thereof of particular interest in accordance with the present invention are characterized as comprising a sequence consisting of at least three contiguous amino acids of groups $R^1$–$R^8$ in the sequence of general formula I

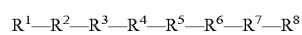

in which $R^1$ and $R^2$ together form a group of formula

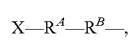

wherein X is H or a one to three peptide group, $R^A$ is suitably selected from Asp, Glu, Asn, Acpc (1-aminocyclopentane carboxylic acid), Ala, Me²Gly, Pro, Bet, Glu(NH₂), Gly, Asp(NH₂) and Suc, $R^B$ is suitably selected from Arg, Lys, Ala, Orn, Ser(Ac), Sar, D-Arg and D-Lys;

$R^3$ is selected from the group consisting of Val, Ala, Leu, norLeu, Ile, Gly, Pro, Aib, Acpc, Lys, and Tyr;

$R^4$ is selected from the group consisting of Tyr, Tyr(PO₃)₂, Thr, Ser, homoSer, Ala, and azaTyr;

$R^5$ is selected from the group consisting of Ile, Ala, Leu, norLeu, Val and Gly;

$R^6$ is His, Arg or 6-NH₂-Phe;

$R^7$ is Pro or Ala; and $R^8$ is selected from the group consisting of Phe, Phe(Br), Ile and Tyr, excluding sequences including $R^4$ as a terminal Tyr group.

Compounds falling within the category of AT2 agonists useful in the practice of the invention include the AII analogues set forth above subject to the restriction that $R^6$ is p-NH₂-Phe. In addition to peptide agents, various nonpeptidic agents (e.g., peptidomimetics) having the requisite AT2 agonist activity are further contemplated for use in accordance with the present invention.

Particularly preferred combinations for $R^A$ and $R^B$ are Asp-Arg, Asp-Lys, Glu-Arg and Glu-Lys. Particularly preferred embodiments of this class include the following: AII, AIII or AII(2–8), Arg-Val-Tyr-Ile-His-Pro-Phe [SEQ ID NO:2]; AII(3–8), also known as des1-AIII or AIV, Val-Tyr-Ile-His-Pro-Phe [SEQ ID NO:3]; AII(1–7), Asp-Arg-Val-Tyr-Ile-His-Pro [SEQ ID NO:4]; AII(2–7). Arg-Val-Tyr-Ile-His-Pro [SEQ ID NO:5]; AII(3–7), Val-Tyr-Ile-His-Pro [SEQ ID NO:6]; AII(5–8), Ile-His-Pro-Phe [SEQ ID NO:7]; AII(1–6), Asp-Arg-Val-Tyr-Ile-His [SEQ ID NO:8]; AII (1–5), Asp-Arg-Val-Tyr-Ile [SEQ ID NO:9]; AII(1–4), Asp-Arg-Val-Tyr [SEQ ID NO:10]; and AII(1–3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr-Ile-His-Pro-Phe [SEQ ID NO:31]. AII(6–8), His-Pro-Phe [SEQ ID NO:14] and AII(4–8), Tyr-Ile-His-Pro-Phe [SEQ ID NO:15] were also tested and found not to be effective.

A class of particularly preferred compounds in accordance with the present invention consists of those with the following general structure:

R1-Arg-R2-R3-R4-His-Pro-R5 wherein R1 is selected from the group consisting of H and Asp;

R2 is selected from the group consisting of Val and Pro;

R3 is selected from the group consisting of Tyr and Tyr(PO₃)₂;

R4 is selected from the group consisting of Ala, Ile, Leu, and norLeu; and

R5 is Phe, Ile, or is absent.

Particularly preferred embodiment of this class are selected from the group consisting of SEQ ID NO:1, SEQ ID NO:4, SEQ ID NO:18, SEQ ID NO:26, SEQ ID NO:31, SEQ ID NO:32, SEQ ID NO:34, and SEQ ID NO:38

Another class of compounds of particular interest in accordance with the present invention are those of the general formula II $R^2$—$R^3$—$R^4$—$R^5$—$R^6$—$R^7$—$R^8$ in which $R^2$ is selected from the group consisting of H, Arg, Lys, Ala, Orn, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, Tyr(PO₃)₂, Thr, Ser, homoSer and azaTyr;

$R^5$ is selected from the group consisting of Ile, Ala, Leu, norLeu, Val and Gly;

$R^6$ is His, Arg or 6-NH₂-Phe;

$R^7$ is Pro or Ala; and $R^8$ is selected from the group consisting of Phe, Phe(Br), Ile and Tyr.

A particularly preferred subclass of the compounds of general formula II has the formula $R^2$—$R^3$—Tyr-$R^5$—His-Pro-Phe [SEQ ID NO:16]

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:17] and Arg-Val-Tyr-Ala-His-Pro-Phe [SEQ ID NO:18]. The fragment AII(4–8) was ineffective in repeated tests; this is believed to be due to the exposed tyrosine on the N-terminus.

In the above formulas, the standard three-letter abbreviations for amino acid residues are employed. In the absence of an indication to the contrary, the L-form of the amino acid is intended. Other residues are abbreviated as follows:

TABLE 1

Abbreviation for Amino Acids

| | |
|---|---|
| Me²Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |

It has been suggested that AII and its analogues adopt either a gamma or a beta turn (Regoli, et al., *Pharmacological Reviews* 26:69 (1974). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Val, Ala, Leu, norLeu, Ile, Gly, Pro, Aib, Acpc and Tyr. In another preferred embodiment, $R^3$ is Lys.

With respect to $R^4$, conformational analyses have suggested that the side chain in this position (as well as in $R^3$ and $R^5$) contribute to, a hydrophobic cluster believed to be essential for occupation and stimulation of receptors. Thus, $R^4$ is preferably selected from Tyr, Thr, Tyr $(PO_3)_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra). In a further preferred embodiment, $R^4$ is Ala.

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, Gly and Val.

In the AI, AI analogues, AI fragments and analogues thereof, AII, AII analogues, fragments and analogues of fragments of particular interest in accordance with the present invention, $R^6$ is His, Arg or 6-NH$_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro in order to provide the most desirable orientation of $R^8$. In position $R^8$, both a hydrophobic ring and an anionic carboxyl terminal appear to be particularly useful in binding of the analogues of interest to receptors; therefore, Tyr and especially Phe are preferred for purposes of the present invention.

Analogues of particular interest include the following:

TABLE 2

Angiotensin II Analogues

| All Analogue Name | Amino Acid Sequence | Sequence Identifier |
|---|---|---|
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SEQ ID NO: 20 |
| Analogue 3 | Ala-Pro-Gly-Asp-Arg-Ile-Tyr-Val-His-Pro-Phe | SEQ ID NO: 21 |
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID NO: 26 |
| Analogue 9 | Asp-Arg-Val-Tyr-Ile-Arg-Pro-Phe | SEQ ID NO: 27 |
| Analogue 10 | Asp-Arg-Val-Tyr-Ile-His-Ala-Phe | SEQ ID NO: 28 |
| Analogue 11 | Asp-Arg-Val-Tyr-Ile-His-Pro-Tyr | SEQ ID NO: 29 |
| Analogue 12 | Pro-Arg-Val-Tyr-Ile-His-Pro-Phe | SEQ ID NO: 30 |
| Analogue 13 | Asp-Pro-Tyr-Ile-His-Pro-Phe | SEQ ID NO: 31 |
| Analogue 14 | Asp-Arg-Val-Tyr(PO$_3$)$_2$-Ile-His-Pro-Phe | SEQ ID NO: 32 |
| Analogue 15 | Asp-Arg-norLeu-Tyr-Ile-His-Pro-Phe | SEQ ID NO: 33 |
| Analogue 16 | Asp-Arg-Val-Tyr-norLeu-His-Pro-Phe | SEQ ID NO: 34 |
| Analogue 17 | Asp-Arg-Val-homoSer-Tyr-Ile-His-Pro-Phe | SEQ ID NO: 35 |

The polypeptides of the instant invention may be synthesized by methods such as those set forth in J. M. Stewart and J. D. Young, *Solid Phase Peptide Synthesis,* 2nd ed., Pierce Chemical Co., Rockford, Ill. (1984) and J. Meienhofer, *Hormonal Proteins and Peptides,* Vol. 2, Academic Press, New York, (1973) for solid phase synthesis and E. Schroder and K. Lubke, *The Peptides,* Vol. 1, Academic Press, New York, (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

In one aspect, the present invention provides methods and kits for the mitigation of tissue damage due to radiation exposure comprising the administration of angiotensinogen, angiotensin I (AI), AI analogues, AI fragments and analogues thereof, angiotensin II (AII), AII analogues, AII fragments or analogues thereof or AII AT$_2$ type 2 receptor agonists (the "active agents").

In another aspect, the present invention provides improved methods and kits for treating a patient afflicted with a neoplastic disease state that is being treated with ionizing or nonionizing radiation, the improvement comprising conjunctive therapy whereby an effective radioprotective amount of the active agents is provided.

In another aspect, the present invention provides improved methods and kits for treating a patient in need of radiation therapy, the improvement comprising the administration of the active agents in conjunction with the radiation therapy.

The invention is appropriate for use with any type of ionizing radiation exposure such as therapeutic or accidental X-ray, gamma ray, or beta particle exposure. Examples of ionizing radiation exposure suitable for treatment with the methods and kits of the present invention include, but are not limited to, clinical radiation therapy, medical diagnostics using radioactive tracers, exposure to naturally occurring ionizing radiation sources such as uranium and radon, wartime exposure, and accidental exposures including occupational exposure at nuclear power facilities, and medical and research institutions. Examples of nonionizing radiation exposure suitable for treatment with the methods and kits of the present invention include, but are not limited to, ultraviolet light, X-rays, microwaves, radio-frequency waves, and electromagnetic radiation.

Virtually any tissue susceptible to radiation-induced tissue damage can gain protection by use of the active agents of the invention. For example, breast tissue is an excellent candidate for receiving the benefit of the subject invention. Radiation-induced tissue damage can be a fatal side effect of over-exposure to radiation therapy. Typically, the fibrotic reaction common in normal breast tissue surrounding the cancerous tumor being treated with radiation therapy undermines the cosmetic advantages of radiation therapy over surgical treatment. This disadvantage will lead many patients to elect a less effective or more dangerous treatment after radiation therapy.

The present invention is also particularly suitable for those patients in need of repeated or high doses of radiation therapy. For some cancer patients, hematopoietic toxicity frequently limits the opportunity for radiation dose escalation (Watanabe et al., *British J. Haematol.* 94:619–627 (1996)). Repeated or high dose cycles of radiation therapy may be responsible for severe stem cell depletion leading to important long-term hematopoietic sequelea and marrow exhaustion. The methods of the present invention provide for improved mortality and blood cell count when used in conjunction with radiation therapy.

Skin exposure is particularly common in accidental radiation exposure. It is an excellent candidate for the inventive therapy, especially as the compounds of the invention can be administered topically. Other tissues that are susceptible to radiation-induced damage following accidental or therapeutic ionizing or nonionizing radiation exposure include, but are not limited to: liver, lung, gastrointestinal tract, kidneys, testes, salivary gland, mucosa and brain.

In another aspect, the present invention provides improved methods and kits for supporting bone marrow transplantation comprising the administration of the active agents to a patient in need thereof. These compounds may be administered in combination with auxiliary agents including, but not limited to interleukin (IL)-3, IL-1, IL-4, Il-5, granulocyte colony stimulating factor (G-CSF), granulocyte-macrophage colony stimulating factor (GM-CSF), macrophage colony stimulating factor (M-CSF), anticancer agents, antiviral agents, and antibiotics.

In a further aspect, the present, invention provides kits for mitigating radiation induced tissue damage and improving the efficacy of radiation therapy, wherein the kits comprise an effective amount of the active agents of the invention for mitigating radiation induced tissue damage or improving the efficacy of radiation therapy, and instructions for using the amount effective of active agent as a therapeutic. In a preferred embodiment, the kit further comprises a pharmaceutically acceptable carrier, such as those adjuvants described above. In another preferred embodiment, the kit further comprises a means for delivery of the active agent to a patient. Such devices include, but are not limited to syringes, material or micellar solutions, bandages, wound dressings, aerosol sprays, lipid foams, transdermal patches, topical administrative agents, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols. The means for delivery may either contain the effective amount of angiotensinogen, AI, AI analogues, AI fragments and analogues thereof, AII, AII analogues, AII fragments or analogues thereof or AII $AT_2$ type 2 receptor agonists, or may be separate from the compounds, which are then applied to the means for delivery at the time of use.

The methods and kits of the present invention, by mitigating radiation induced tissue damage and improving the efficacy of radiation therapy and bone marrow transplantation, significantly enhance the utility of presently available treatments both for radiation-induced tissue damage and for clinical radiation therapy.

In a further aspect of the present invention, a method of increasing megakaryocyte production and mobilization and platelet production by exposure to the active agents of the inventions is disclosed. In one embodiment, megakaryocytes are isolated from bone marrow as described in U.S. Pat. No. 5,178,856, incorporated by reference herein in its entirety. Briefly, marrow is flushed from a subject's femur with Iscove's modification of Dulbecco's medium (IMDM) supplemented with Nutridoma-SP (Boehringer Mannheim, Indianapolis, Ind.), a serum-free medium supplement. For culture studies, a single cell suspension is made by repetitive expulsion through progressively smaller needles. For flow cytometry controls, a monocellular suspension is made by gentle filtration through a 100 micron nylon mesh. Preferably, adherent cells are removed to enrich the numbers of megakaryocytes or their progenitor cells. Up to $2 \times 10^6$ cells/ml are placed in growth medium at 37° C. in a humidified atmosphere in the presence of, preferably, between about 0.1 ng/ml and about 10 mg/ml of the active agents. The cells are expanded for a period of between 2 and 21 days and cellular proliferation is assessed at various time points during this time period. Subsequent medium changes are performed as needed. In a preferred embodiment, megakaryocyte production and mobilization and platelet production are assessed by the extent of megakaryocyte ploidization by flow cytometry as described in U.S. Pat. No. 5,155,211, incorporated by reference herein in its entirety. Briefly, the appearance of granules and the extensive surface-connected open canalicular membrane system as well as a substantial decrease in the nucleus:cytoplasm volume distribution, indicates that the megakaryocyte population has completed the process of polyploidization but has not yet generated a major portion of their final complement of platelet-specific cytoplasmic components.

In another embodiment, subjects are irradiated as above and active agent is injected subcutaneously before, at the time of, and after irradiation. Blood samples are taken at various times after administration of the active agent to monitor the number of white blood cells, megakaryocytes and platelets. In a preferred embodiment, subjects are treated with total body irradiation and active agent is administered subcutaneously (10 μg/kg/day or 100 μg/kg/day) at various times before and after irradiation. The number of white blood cells, megakaryocytes and platelets is preferably determined by counting with a hemacytometer followed by differential morphologic analysis.

In another embodiment of this aspect of the invention, hematopoietic precursor cells are isolated from bone marrow, peripheral blood or umbilical cord blood and cultured under appropriate growth conditions, in the presence of the active agents. Megakaryocyte production is assessed at various time points during culture by differential morphologic analysis.

In a preferred embodiment, hematopoietic precursor cells are isolated from bone marrow aspirates from the posterior iliac crest (Caplan and Haynesworth, U.S. Pat. No. 5,486,359). $CD34^+$ hematopoietic precursor cells are isolated from the aspirate by attaching a biotinylated monoclonal antibody specific for CD34 (available from Becton Dickinson, Sunnyvale, Calif., USA) to a streptavidin affinity column (Ceprate SC; CellPro, Bothell, Wash., USA) and passing the aspirate through the column, followed by appropriate column washing and stripping, according to standard techniques in the art. The isolated cells are suspended in culture medium and incubated in the presence of, preferably, between about 0.1 ng/ml and about 10 mg/ml of the active agents of the invention. The cells are expanded for a period of between 8 and 21 days and megakaryocyte production is assessed via phase microscopy to detect increased size and polyploidization at various points during this time period.

In a further embodiment of the present invention, a method of increasing megalcaryocyte production and mobilization and platelet production by exposure to the active agents is disclosed, either in the presence or absence of other growth factors and cytokines. Examples of such growth factors and cytokines include, but are not limited to thrombopoietin, lymphokines, interleukins—1, 2, 3, 4, 5, 6, 7, 8, 9, 10, 11, granulocyte colony-stimulating factor, granulocyte/macrophage colony stimulating factor, macrophage colony-stimulating factor, tumor necrosis factor, epidermal growth factor, fibroblast growth factor, platelet derived growth factor, transforming growth factor beta, and stem cell factor.

In a further preferred embodiment, megakaryocytes and/or platelets that have been cultured in the presence of the active agents are used for autologous transplantation, to reconstitute a depleted hematopoietic system. Prior to transplantation, the cells are rinsed to remove all traces of culture fluid, resuspended in an appropriate medium and then pelleted and rinsed several times. After the final rinse, the cells are resuspended at between $0.7 \times 10^6$ and $50 \times 10^6$ cells per ml in an appropriate medium and reinfused into a subject through intravenous infusions. Following transplantation, subject peripheral blood samples are evaluated for increased megakaryocyte ploidy and platelet number by standard flow cytometry and cell sorting techniques. (Talmadge, et al., supra).

In another aspect of the present invention the active agents are used to increase in vivo megakaryocyte production and mobilization and platelet production. For use in increasing megakaryocyte production and mobilization and platelet production, the active agents may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, intratendinous, intraspinal, intracranial, intrathoracic, infusion techniques or intraperitoneally.

The active agents of all aspects of the present invention may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrasternal, intratendinous, intraspinal, intracranial, intrathoracic, infusion techniques or intraperitoneally.

The active agents of the invention may be made up in a solid form (including granules, powders or suppositories) or in a liquid form (e.g., solutions, suspensions, or emulsions). The compounds of the invention may be applied in a variety of solutions. Suitable solutions for use in accordance with the invention are sterile, dissolve sufficient amounts of the peptide, and are not harmful for the proposed application. In this regard, the compounds of the present invention are very stable but are hydrolyzed by strong acids and bases. The compounds of the present invention are soluble in organic solvents and in aqueous solutions at pH 5–8.

The active agents may be subjected to conventional pharmaceutical operations such as sterilization and/or may contain conventional adjuvants, such as preservatives, stabilizers, wetting agents, emulsifiers, buffers etc. For administration, the active agents are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Formulations suitable for topical administration include liquid or semi-liquid preparations suitable for penetration through the skin (e.g., liniments, lotions, ointments, creams, or pastes) and drops suitable for administration to the eye, ear, or nose.

The dosage regimen for mitigating radiation-induced tissue damage and improving the efficacy of radiation therapy with the active agents is based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods. Dosage levels of the order of between 0.1 ng/kg and 10 mg/kg body weight of the active agents are useful for all methods of use disclosed herein.

The treatment regime will also vary depending on the disease being treated, based on a variety of factors, including the type of injury, the age, weight, sex, medical condition of the individual, the severity of the condition, the route of administration, and the particular compound employed. For example, the active agents are administered to an oncology patient for up to 30 days prior to a course of radiation therapy and for up to 60 days post-radiation exposure. The therapy is administered for 1 to 6 times per day at dosages as described above.

In all of these embodiments, the compounds of the invention can be administered either prior to, simultaneously with, or subsequent to radiation exposure.

In a preferred embodiment, the active agent is administered subcutaneously. A suitable subcutaneous dose of active ingredient of active agent is preferably between about 0.1 ng/kg and about 10 mg/kg administered twice daily for a time sufficient to mitigate radiation-induced tissue damage, to provide a radioprotective effect for a radiation therapy patient afflicted with a neoplastic disease, to effectively treat a patient in need of radiation therapy, to support bone marrow transplantation and to promote megakaryocyte production and mobilization and platelet production. In a more preferred embodiment, the concentration of active agent is between about 100 ng/kg body weight and about 10.0 mg/kg body weight. In a most preferred embodiment, the concentration of active agent is between about 10 µg/kg body weight and about 10.0 mg/kg body weight. This dosage regimen maximizes the therapeutic benefits of the subject invention while minimizing the amount of agonist or peptide needed. Such an application minimizes costs as well as possible deleterious side effects.

For subcutaneous administration, the active ingredient may comprise from 0.0001% to 10% w/w, e.g., from 1% to 2% by weight of the formulation, although it may comprise as much as 10% w/w, but preferably not more than 5% w/w, and more preferably from 0.1% to 1% of the formulation.

In another preferred embodiment of the present invention, the active agent is administered topically. Suitable topical doses and active ingredient concentration in the formulation are as described for subcutaneous administration.

In a preferred embodiment of all of the aspects of the invention, the active agent is selected from the group consisting of SEQ ID NO. 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO: 34; SEQ ID NO:35, SEQ ID NO:36; and SEQ ID NO:37.

In a further preferred embodiment of the above aspects of the invention, administration of the active agent is localized to the area affected by the tissue-damaging radiation.

In another aspect of the present invention, an improved cell culture medium is provided for megakaryocyte and platelet production, wherein the improvement comprises addition to the cell culture medium of an effective amount of between about 0.1 ng and 10 mg/ml of the active agents of the invention. Any cell culture media that can support megalcaryocyte and platelet production can be used with the present invention. Such cell culture media include, but are not limited to Basal Media Eagle, Dulbecco's Modified Eagle Medium, Iscove's Modified Dulbecco's Medium, McCoy's Medium, Minimum Essential Medium, F-10 Nutrient Mixtures, Opti-MEM® Reduced-Serum Medium, RPMI Medium, and Macrophage-SFM Medium or combinations thereof.

The improved cell culture medium can be supplied in either a concentrated (ie: 10×) or non-concentrated form, and may be supplied as either a liquid, a powder, or a lyophilizate. The cell culture may be either chemically defined, or may contain a serum supplement. Culture media is commercially available from many sources, such as GIBCO BRL (Gaithersburg, Md.) and Sigma (St. Louis, Mo.)

In a further aspect, the present invention provides kits for megakaryocyte and platelet production, wherein the kits comprise an amount effective for megakaryocyte and platelet production of the active agents of the invention, and instructions for its use as a cell culture media supplement.

In a preferred embodiment, the kits further comprise cell culture growth medium. Any cell culture media that can support megakaryocyte and platelet production can be used with the present invention. Examples of such cell culture media are described above. The cell culture medium can be supplied in either a concentrated (ie: 10×) or non-concentrated form, and may be supplied as either a liquid, a powder, or a lyophilizate. The cell culture may be either chemically defined, or may contain a serum supplement.

In a further preferred embodiment, the kit further comprises a sterile container, which can comprise either a sealed container, such as a cell culture flask, a roller bottle, or a centrifuge tube, or a non-sealed container, such as a cell culture plate or microtiter plate (Nunc; Naperville, Ill.).

In another preferred embodiment, the kit further comprises an antibiotic supplement for inclusion in the reconstituted cell growth medium. Examples of appropriate antibiotic supplements include, but are not limited to actimonycin D, Fungizone®, kanamycin, neomycin, nystatin, penicillin, streptomycin, or combinations thereof (GIBCO).

The present invention may be better understood with reference to the accompanying example that is intended for purposes of illustration only and should not be construed to limit the scope of the invention, as defined by the claims appended hereto.

EXAMPLE 1

Effect of AII Ion Rat Mortality and White Blood Cell Recovery After Irradiation

Figure 2:
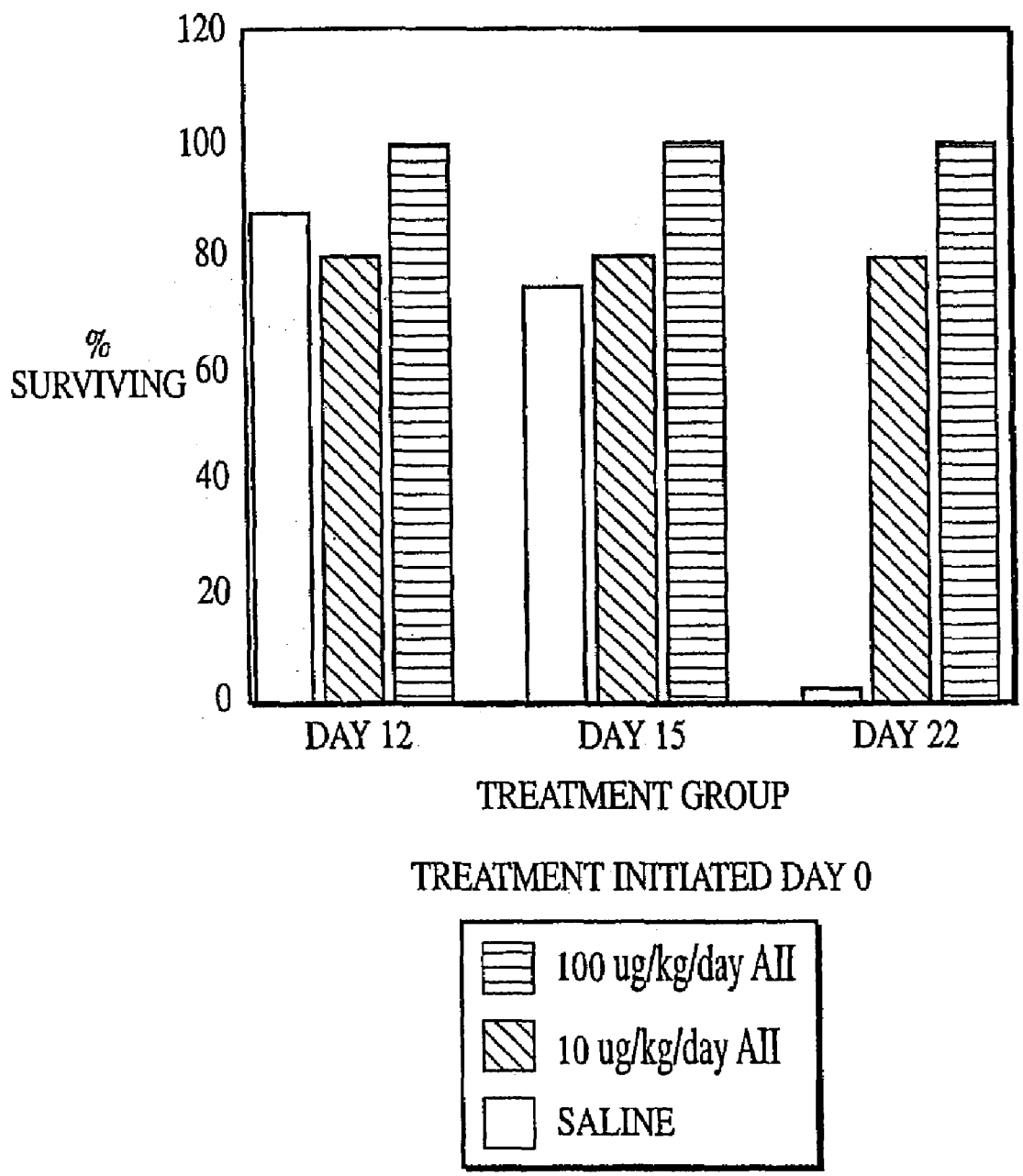
FIG. 2 is a graph showing the effect of AII treatment on the day of exposure on post-irradiation mouse mortality.
Figure 3:
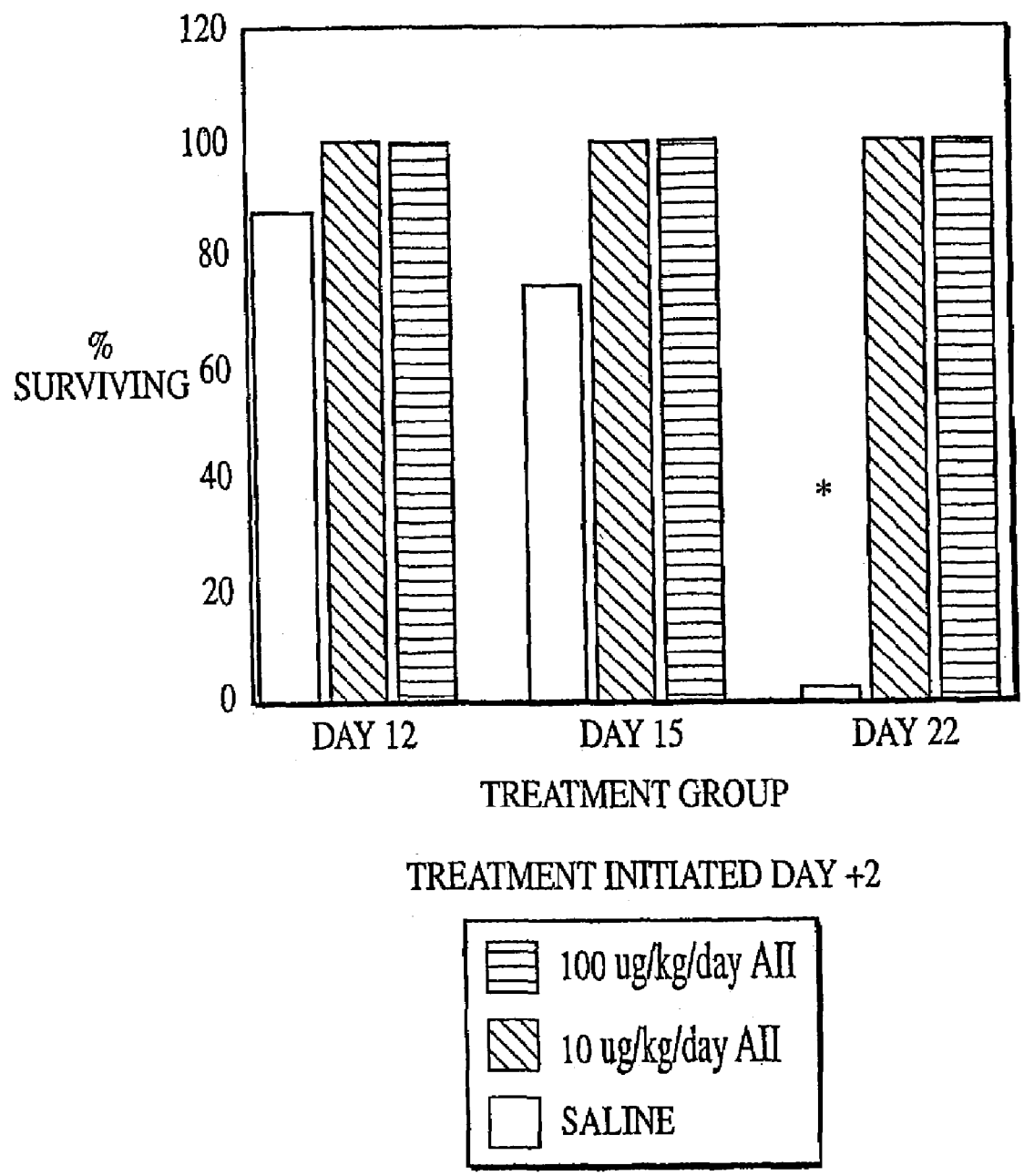
FIG. 3 is a graph showing the effect of AII treatment two days following exposure on post-irradiation mouse mortality.
Figure 4:
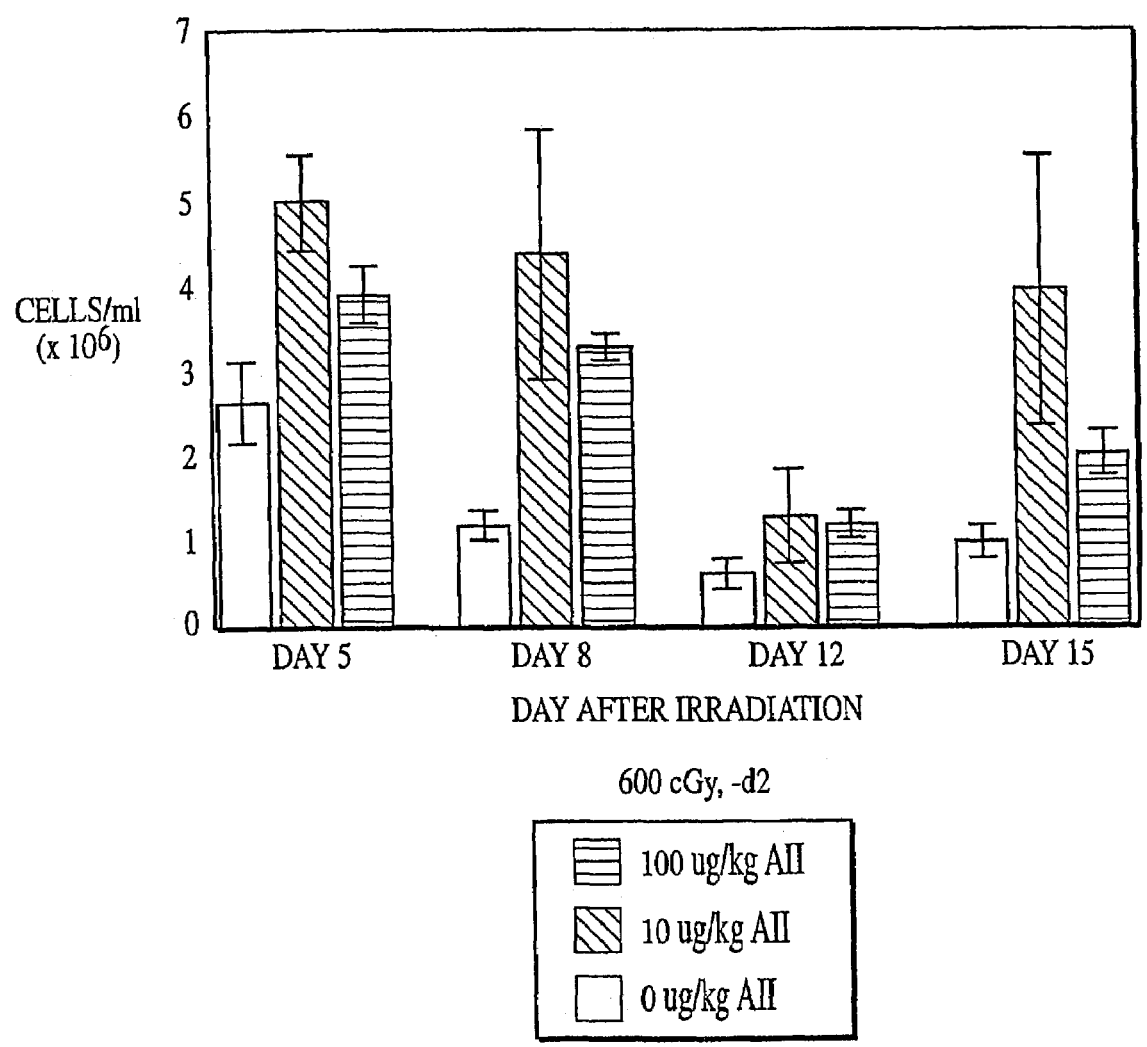
FIG. 4 is a graph showing the effect of AII treatment two days prior to exposure on white blood cell number after irradiation.
Figure 5:
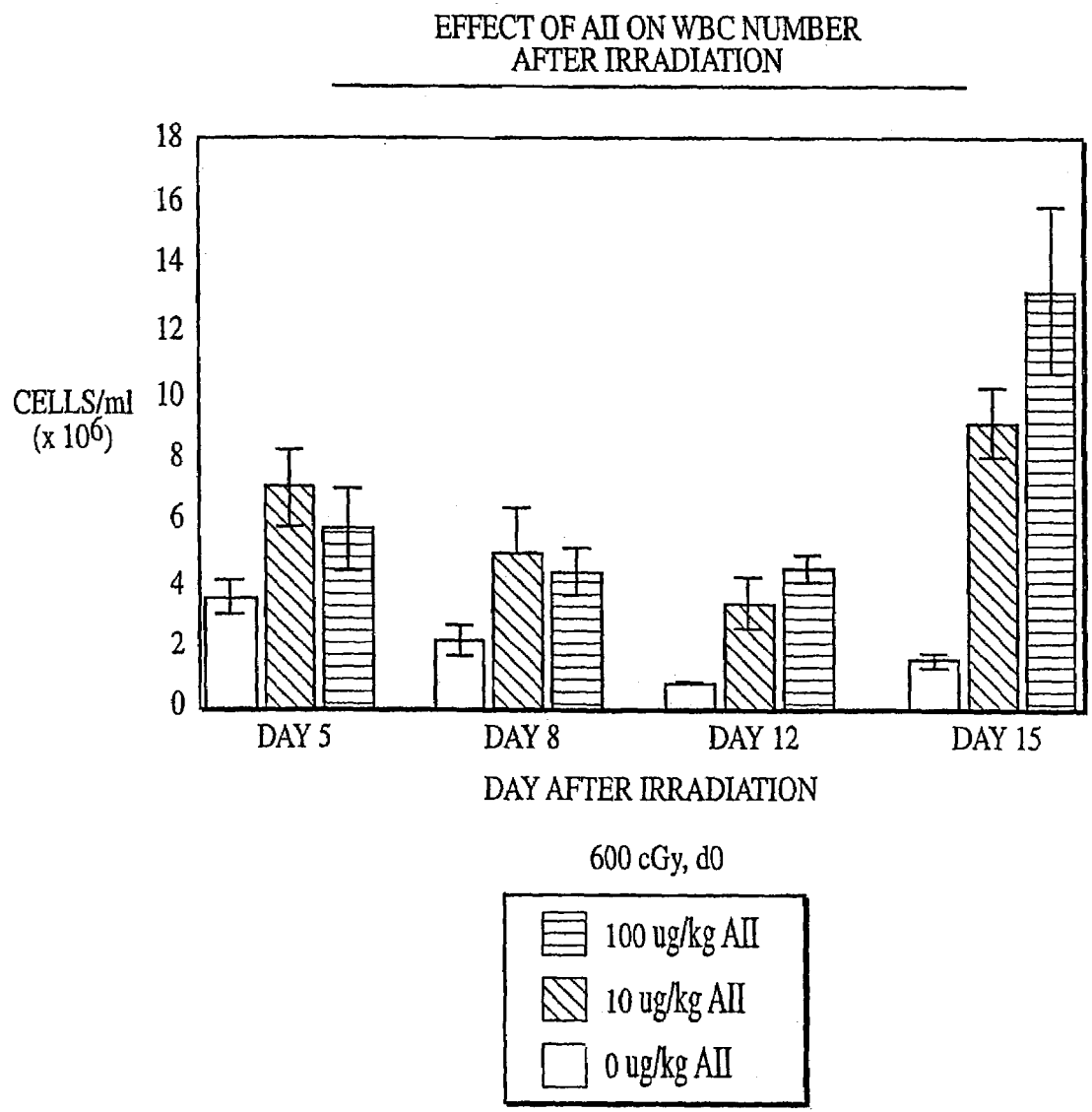
FIG. 5 is a graph showing the effect of AII treatment on the day of exposure on white blood cell number after irradiation.
Figure 6:
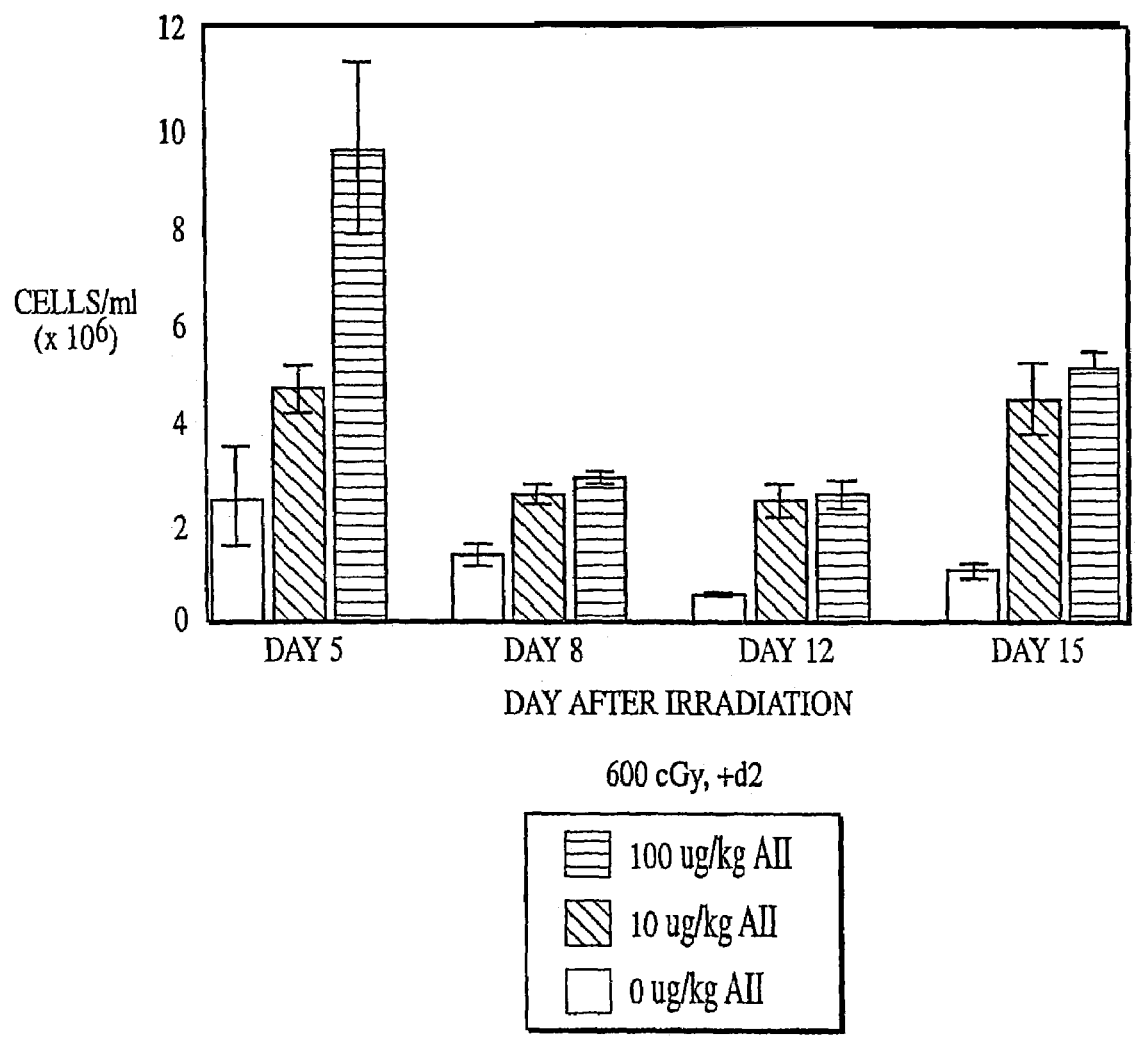
FIG. 6 is a graph showing the effect of AII treatment two days following exposure on white blood cell number after irradiation.
Figure 7:
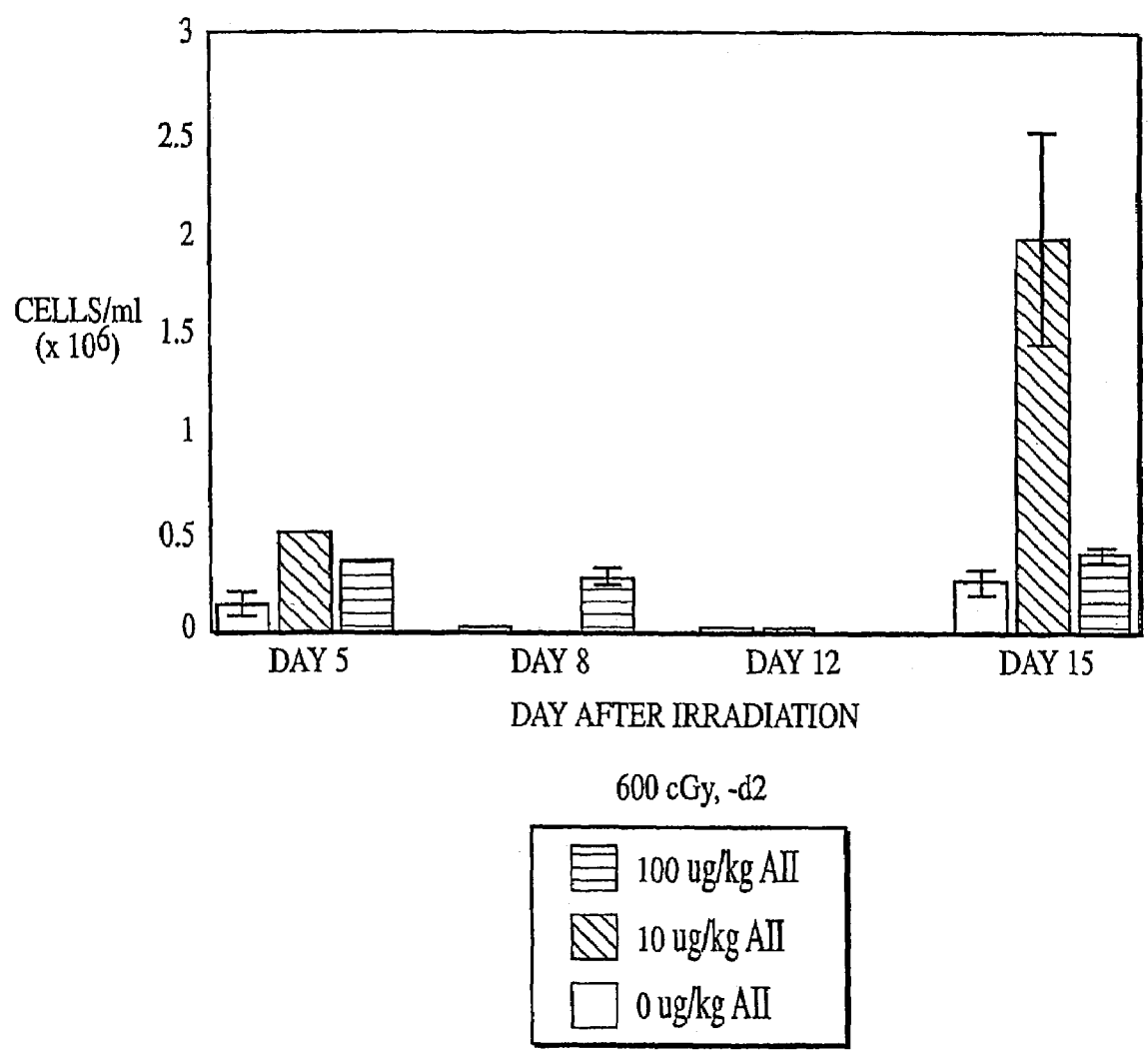
FIG. 7 is a graph showing the effect of AII treatment two days prior to exposure on megakaryocyte number after irradiation.
Figure 8:
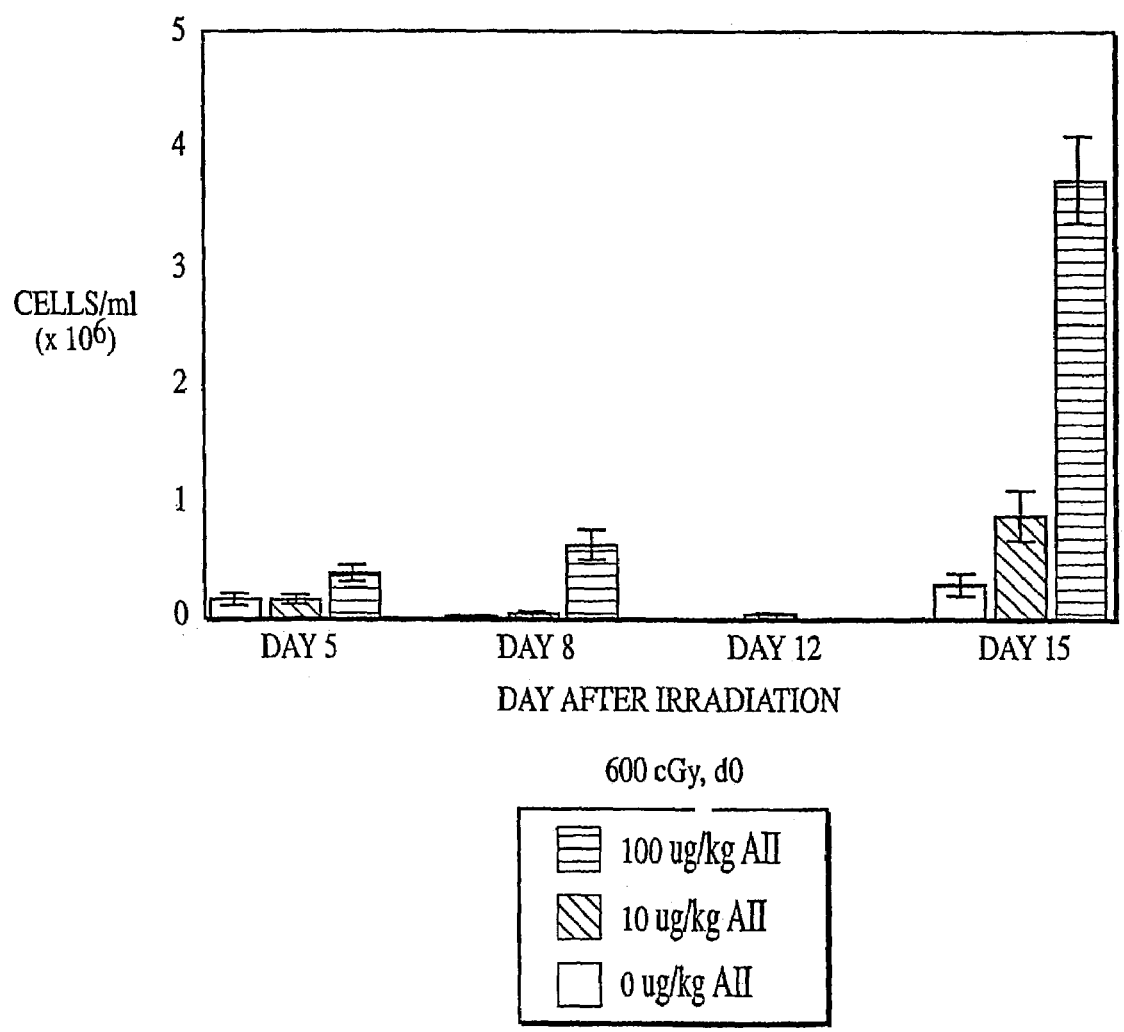
FIG. 8 is a graph showing the effect of AII treatment on the day of exposure on megakaryocyte number after irradiation.
Figure 9:
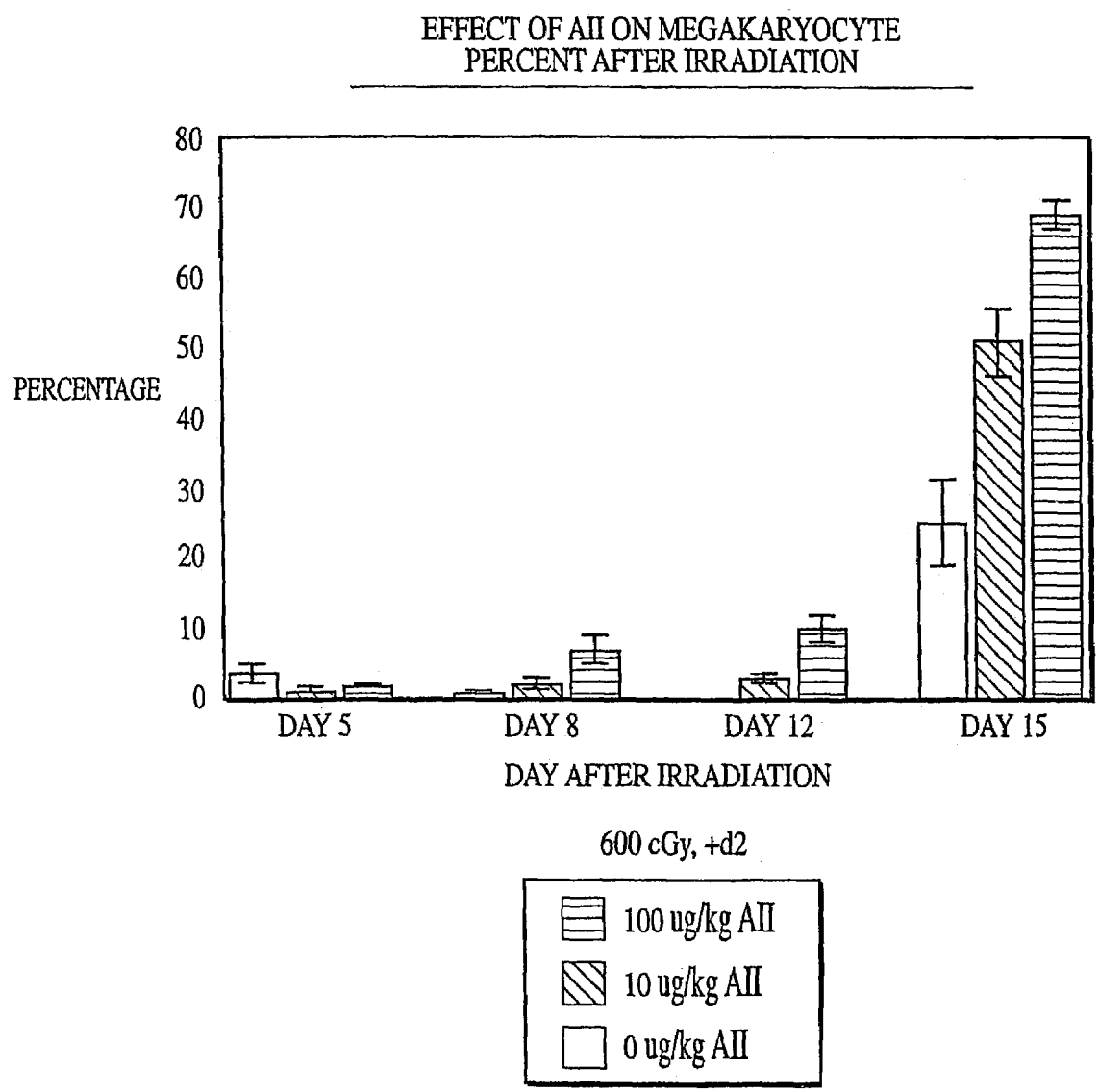
FIG. 9 is a graph showing the effect of AII treatment two days following exposure on megakaryocyte percentage after irradiation.
Figure 10:
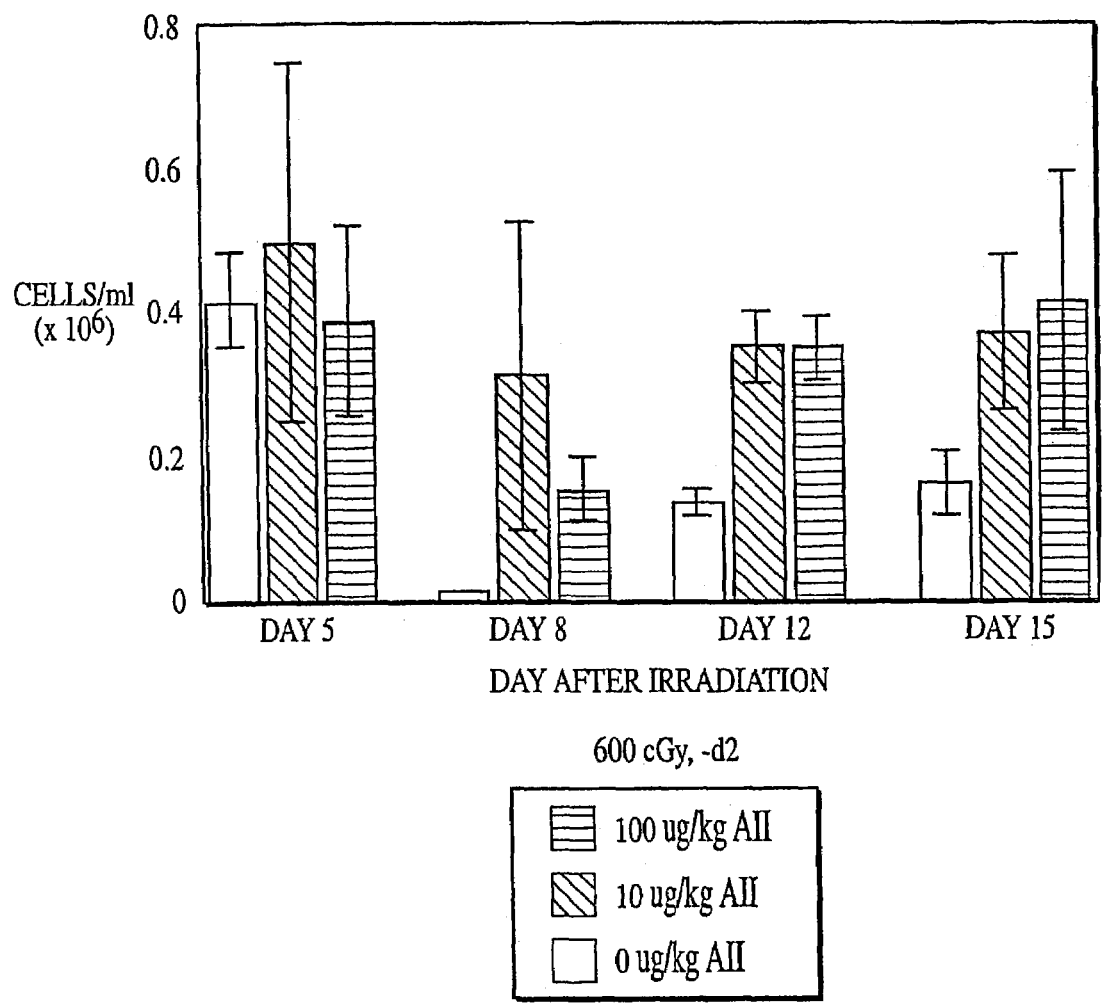
FIG. 10 is a graph showing the effect of AII treatment two days prior to exposure on monocyte number after irradiation.
Figure 11:
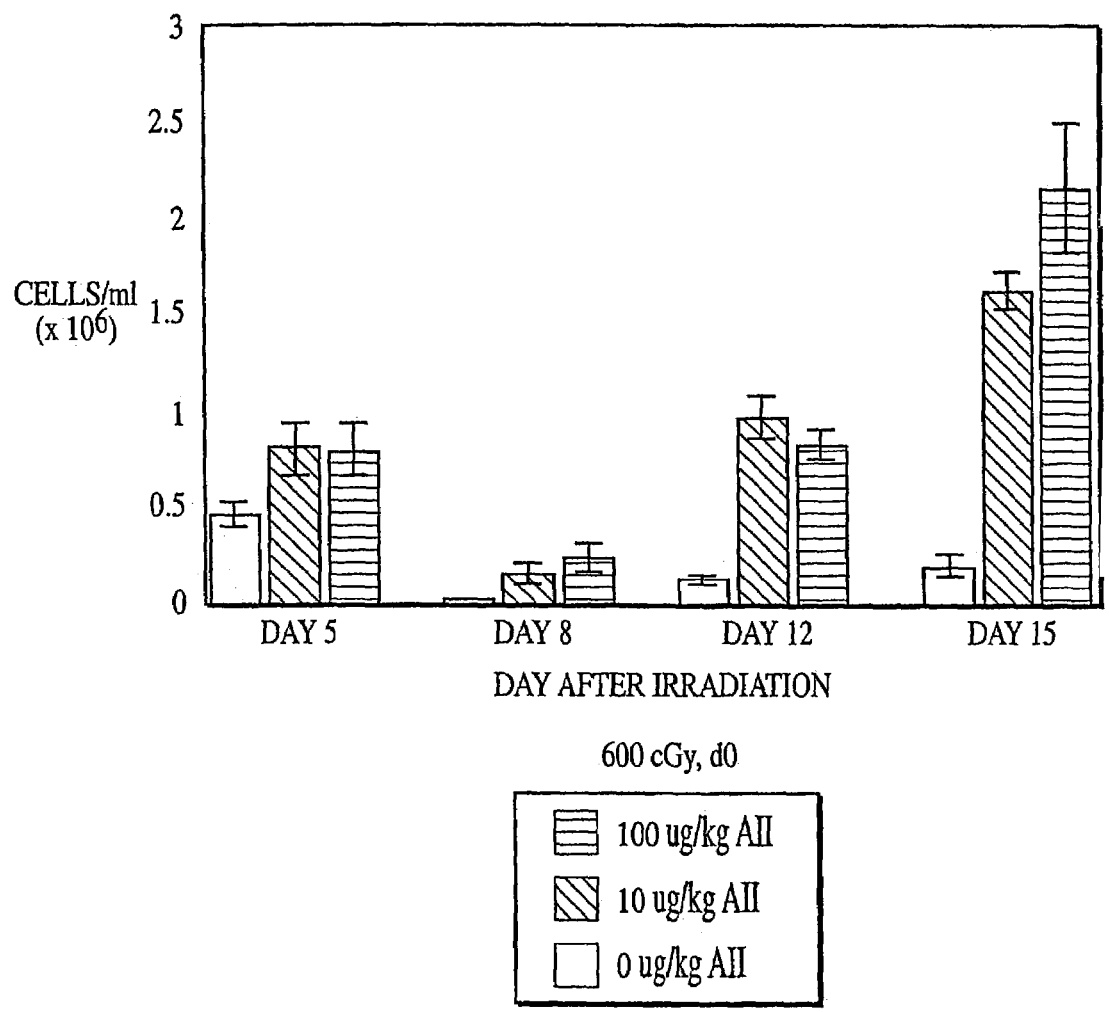
FIG. 11 is a graph showing the effect of AII treatment on the day of exposure on monocyte number after irradiation.
Figure 12:
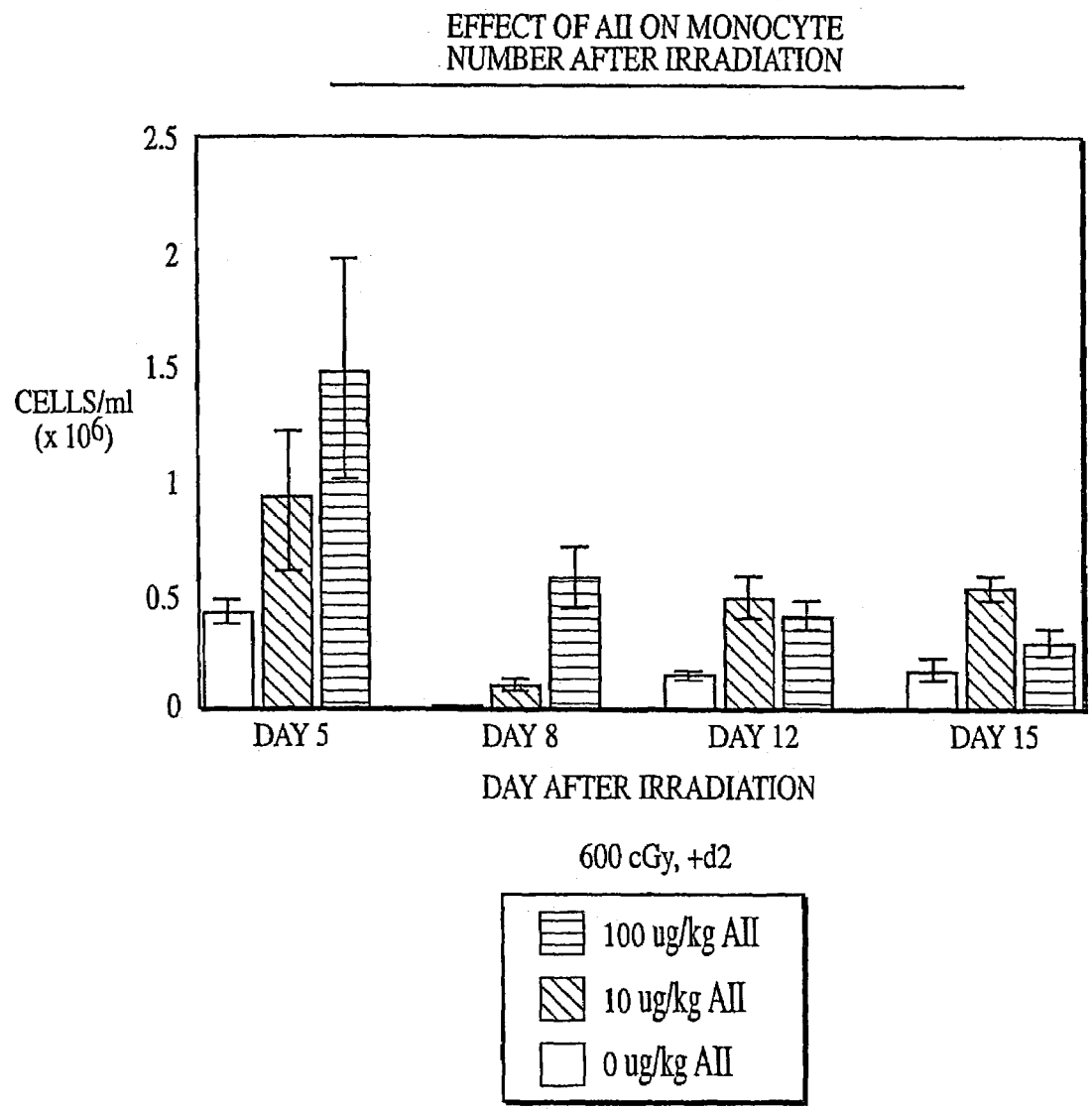
FIG. 12 is a graph showing the effect of AII treatment two days following exposure on monocyte number after irradiation.
Figure 13:
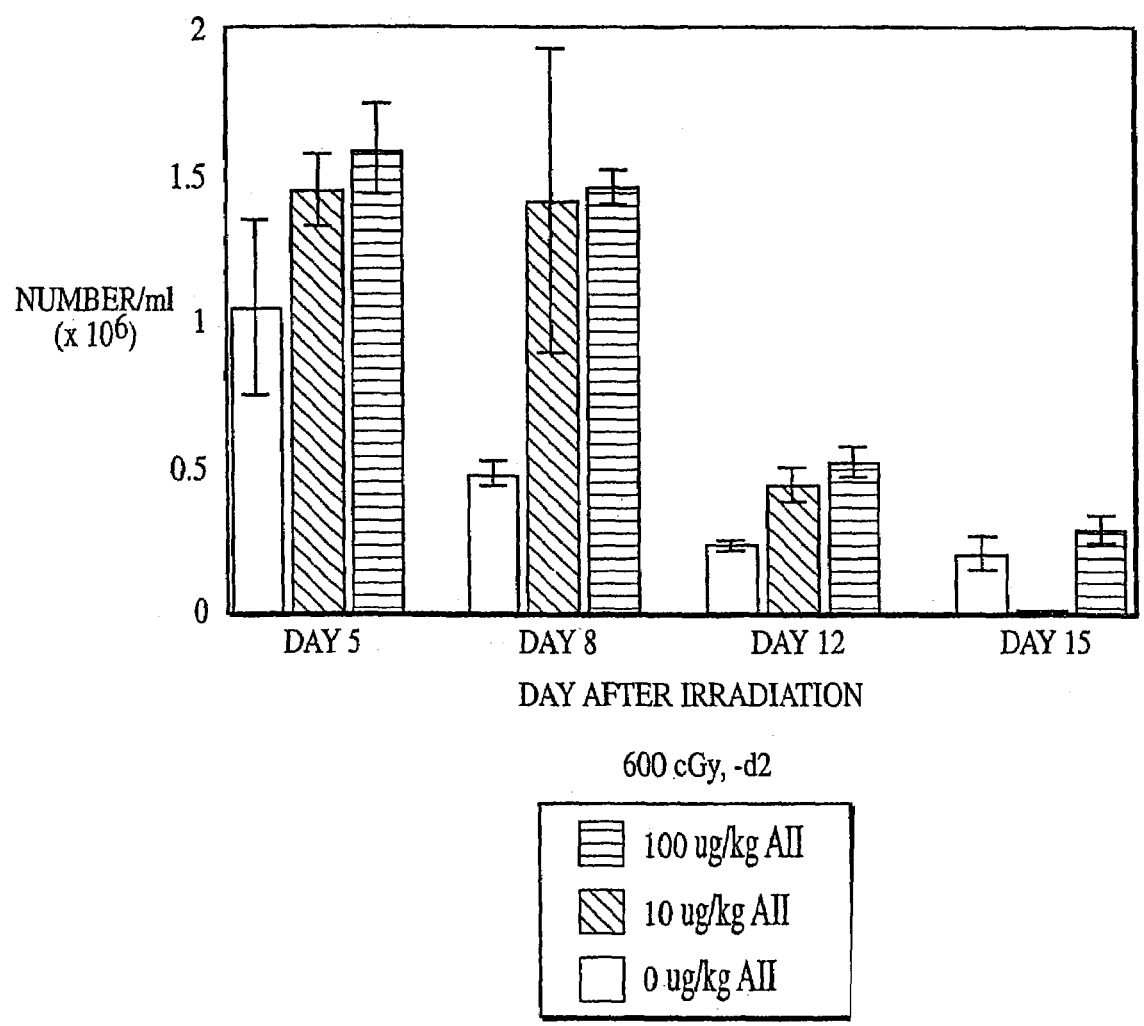
FIG. 13 is a graph showing the effect of AII treatment two days prior to exposure on neutrophil number after irradiation.
Figure 14:
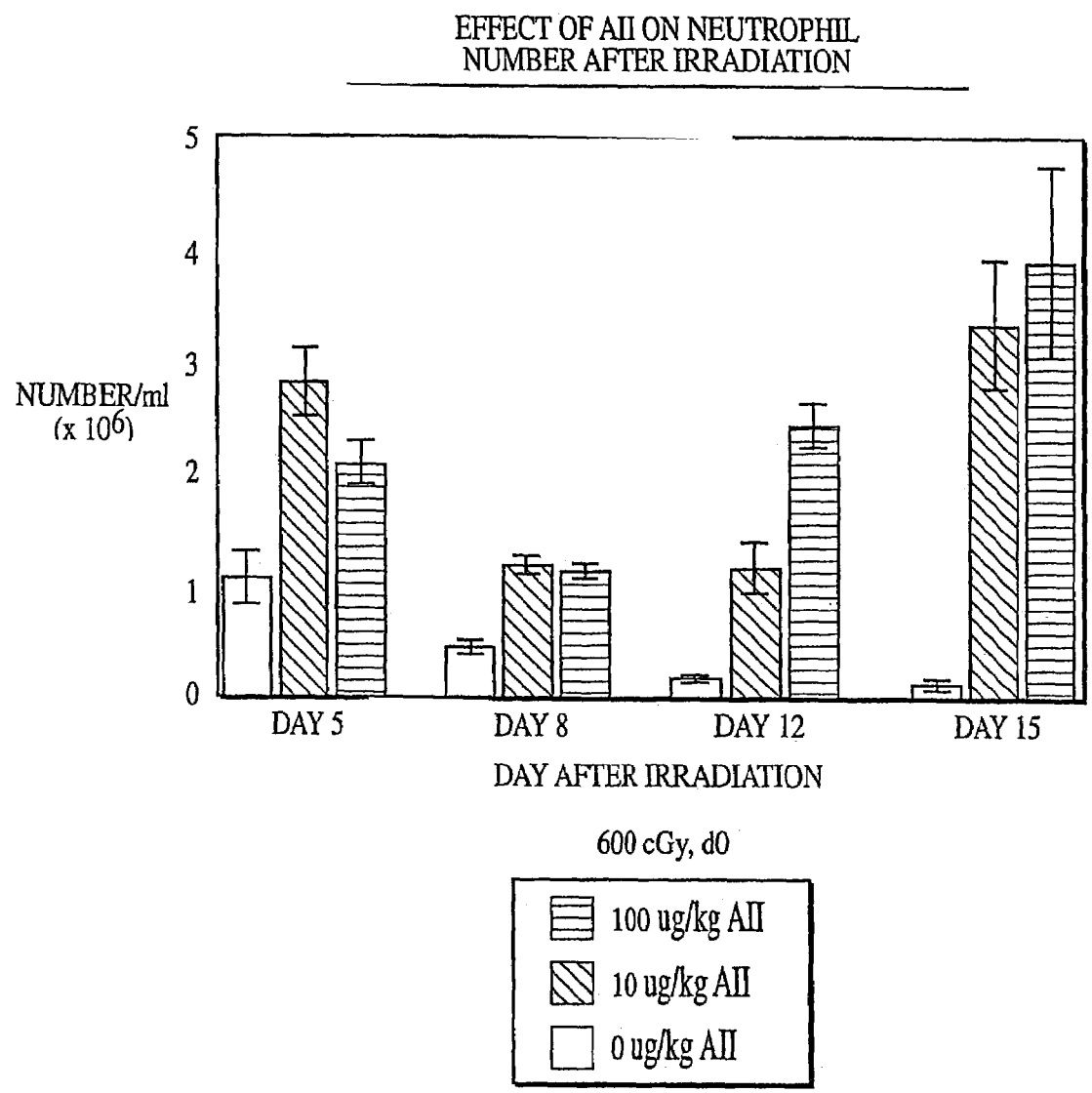
FIG. 14 is a graph showing the effect of AII treatment on the day of exposure on neutrophil number after irradiation.
Figure 15:
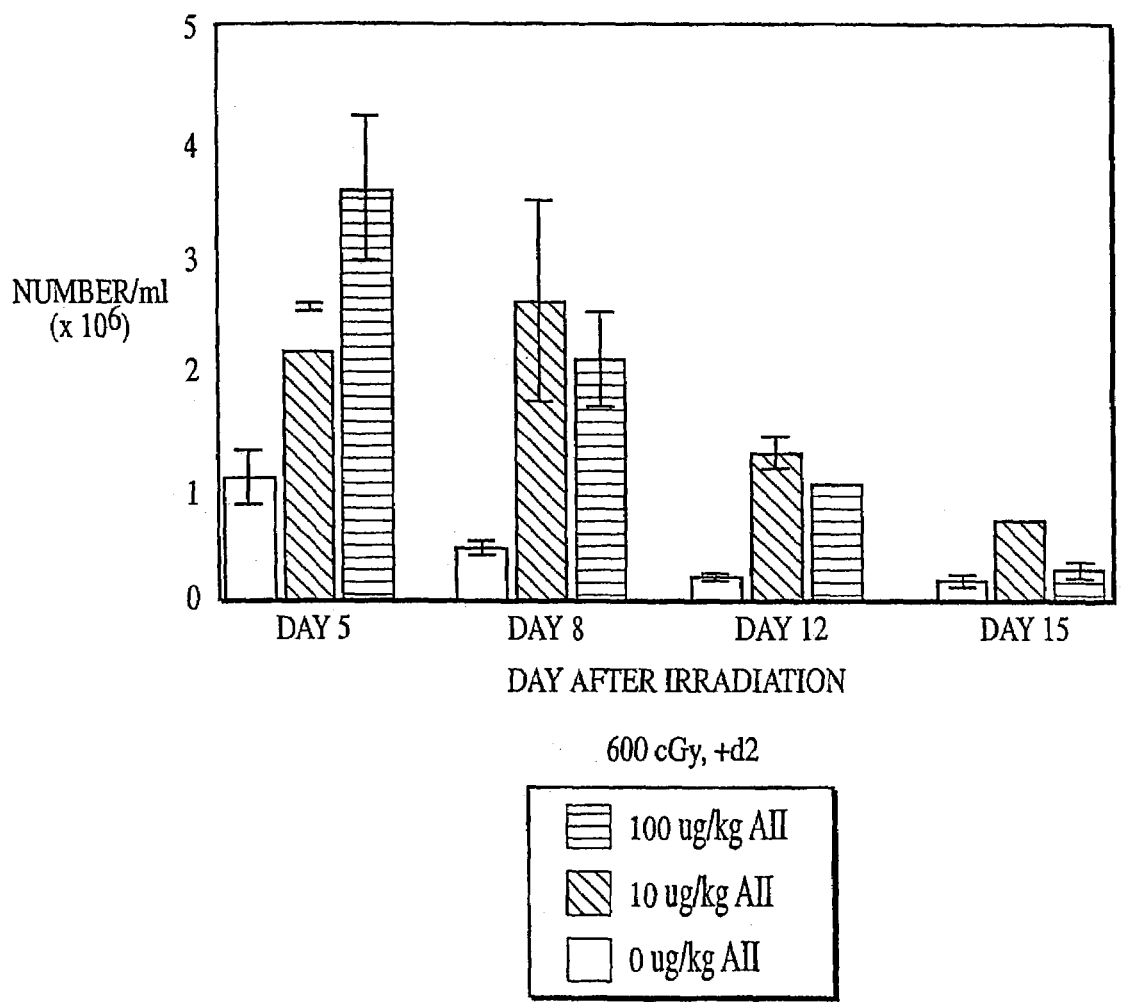
FIG. 15 is a graph showing the effect of AII treatment two days following exposure on neutrophil number after irradiation.
Figure 16:
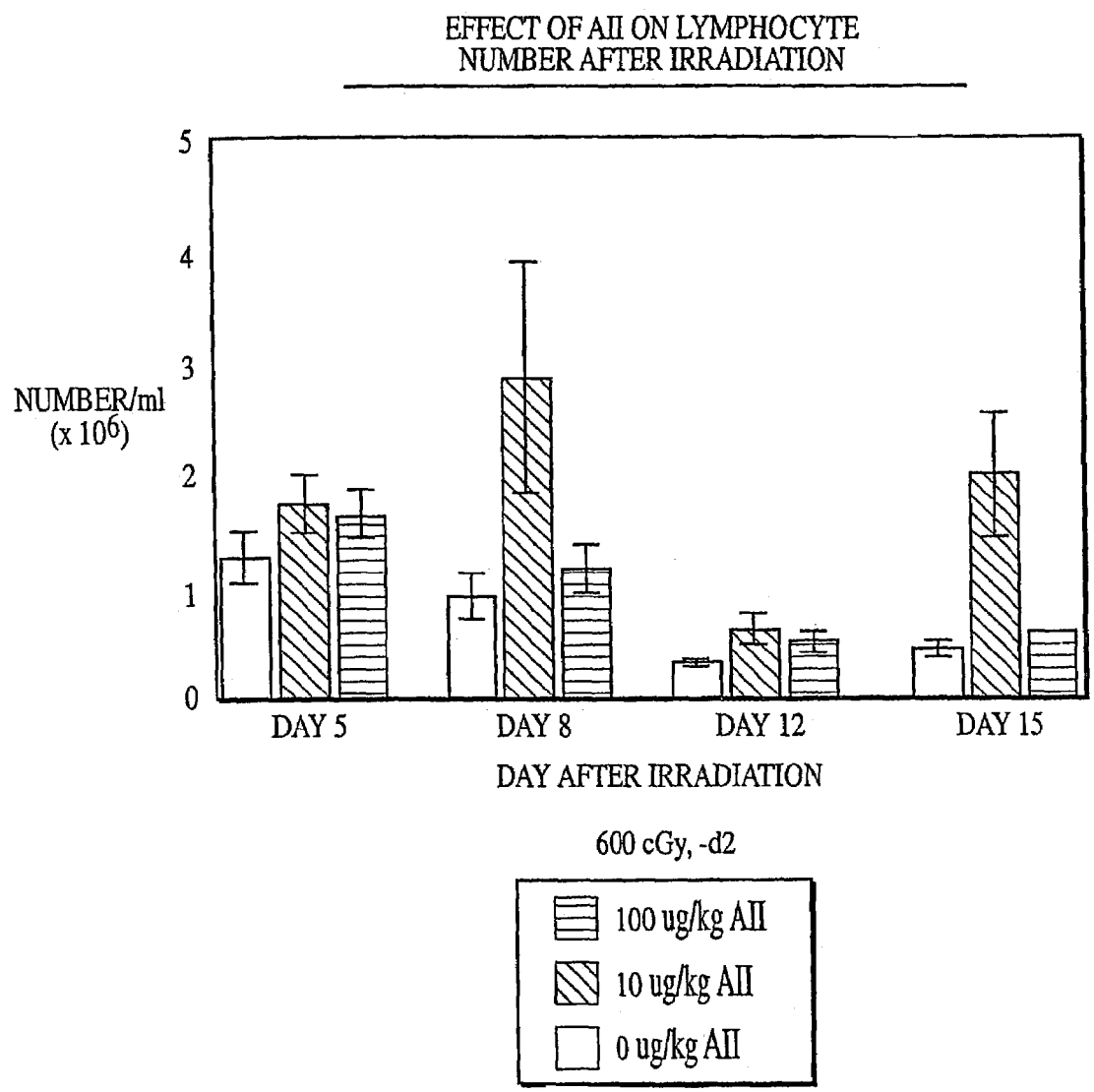
FIG. 16 is a graph showing the effect of AII treatment two days prior to exposure on lymphocyte number after irradiation.
Figure 17:
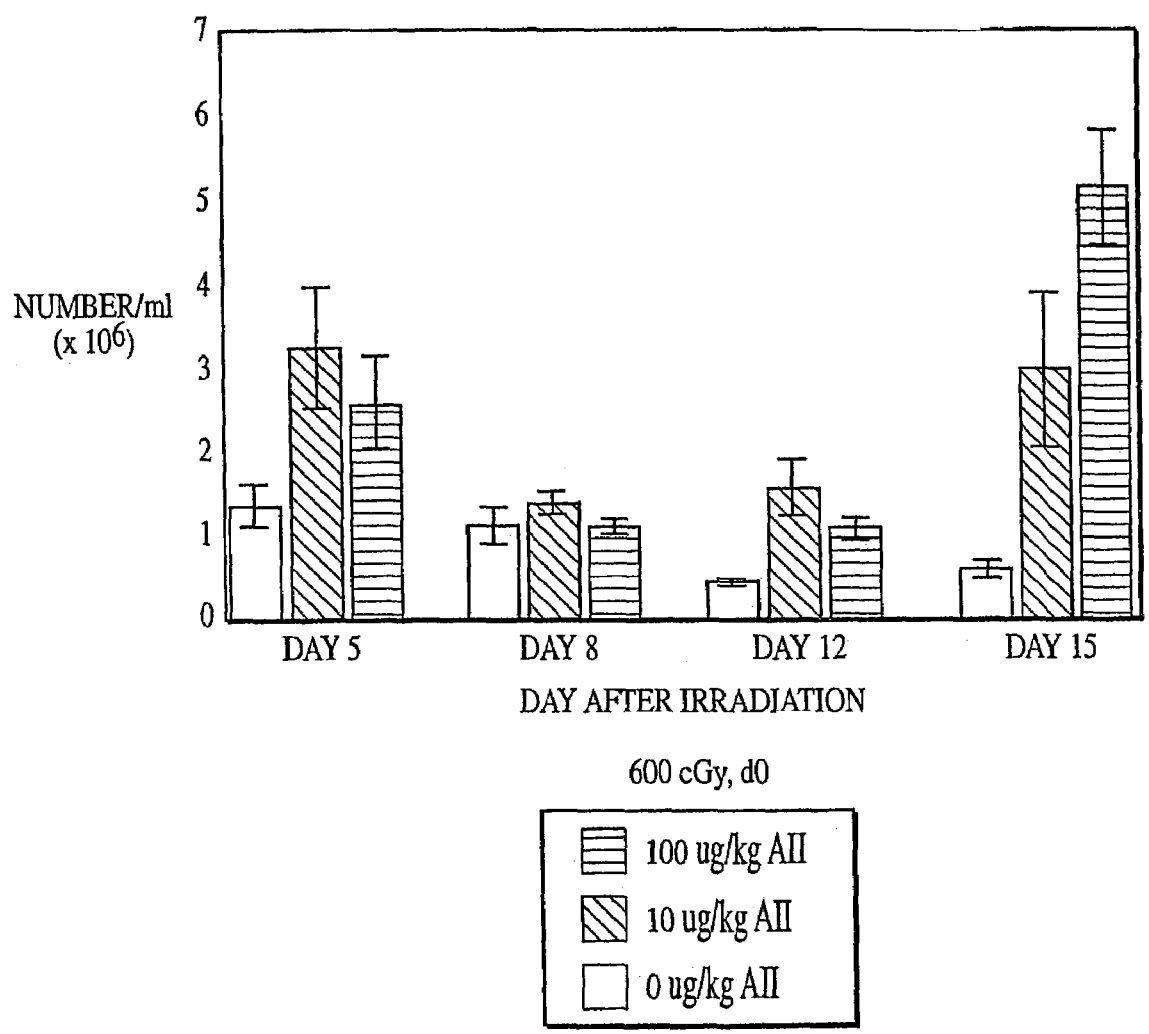
FIG. 17 is a graph showing the effect of AII treatment on the day of exposure on lymphocyte number after irradiation.
Figure 18:
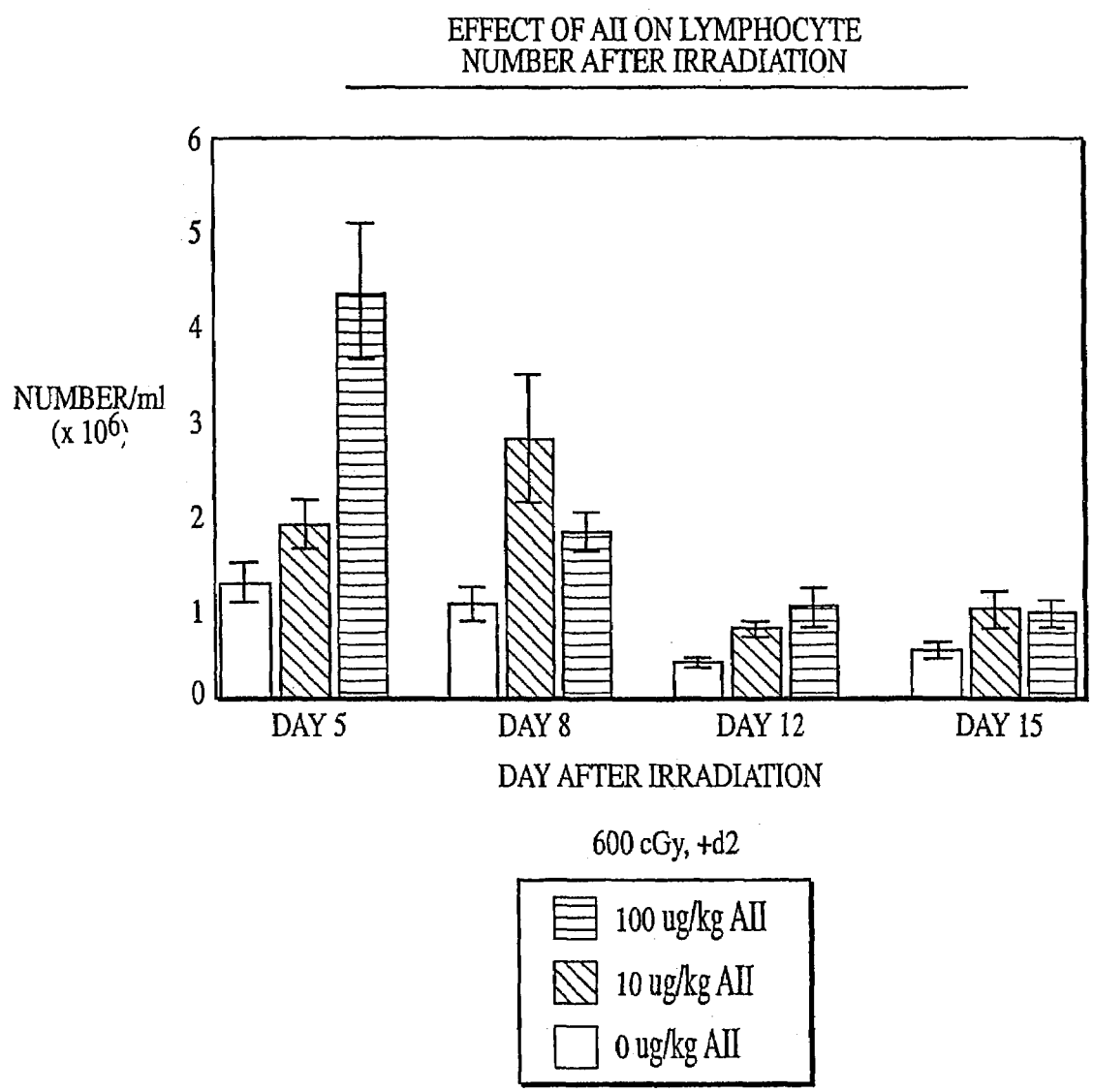
FIG. 18 is a graph showing the effect of AII treatment two days following exposure on lymphocyte number after irradiation.
Figure 19:
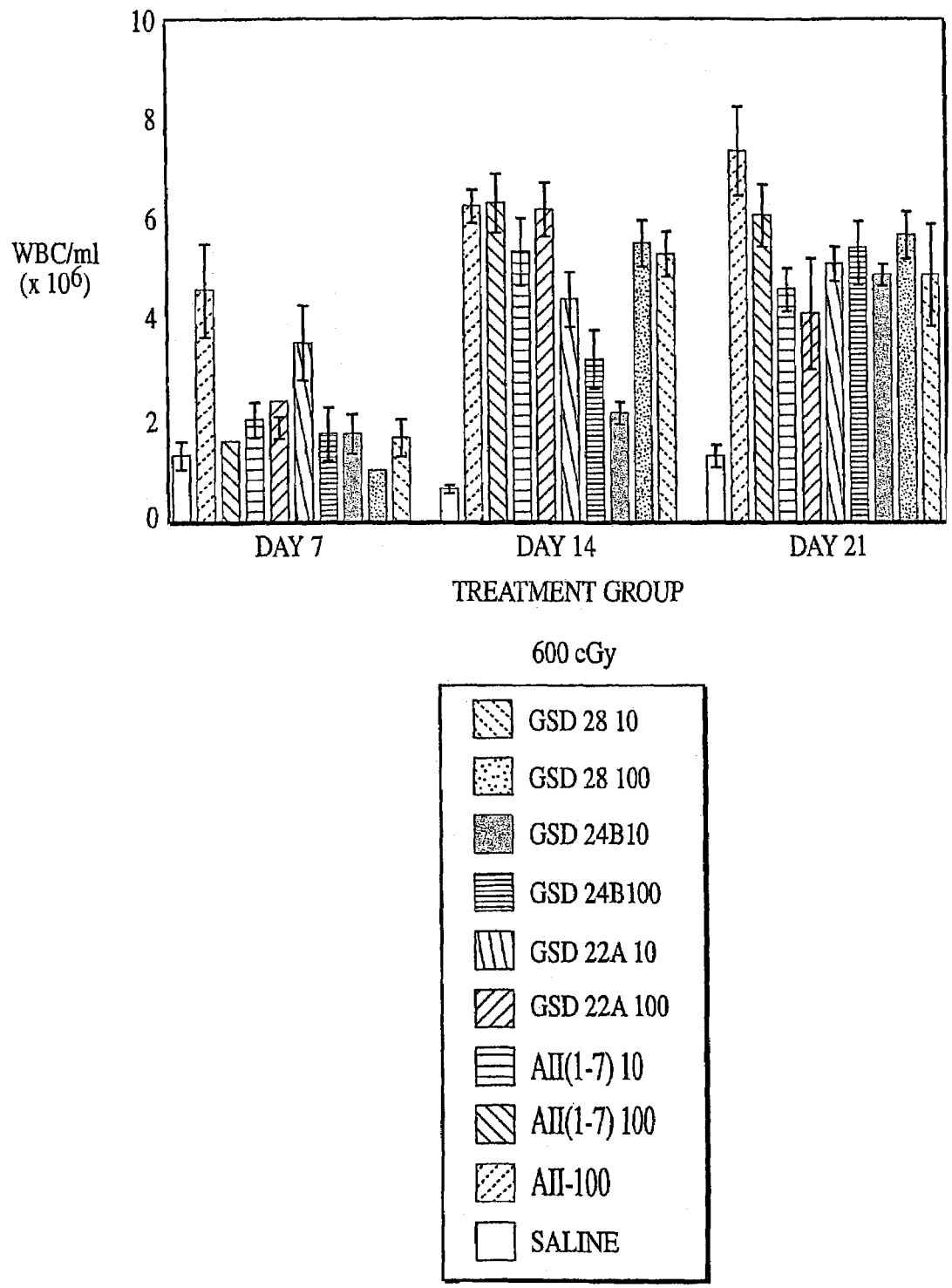
FIG. 19 is a graph showing is a graph showing the effect of AII analogues and fragments treatment on white blood cell number after irradiation.

Female C57B1/6 mice (Jackson Labs, Bar Harbor, Me.) were irradiated with 600 cGy total body irradiation. Subcutaneous injection with either AII (10 μg/kg/day or 100 μg/kg/day) or saline (placebo) was initiated two days before (−day 2), on the day of (day 0) or 2 days after (+day 2) irradiation and continued until the animals succumbed to the irradiation or were necropsied. At various times after irradiation, the mice were anaesthetized with Metofane (Pittman-Moore Animal Health, NZ) and bled via the retro-orbital sinus. Red blood cells were lysed with 0.3% acetic acid and the number of white blood cells was determined by counting with a hemacytometer. The data in FIGS. 1–3 show that administration of AII starting at two days prior to irradiation did not protect against mortality resulting from irradiation (FIG. 1), but that AII administration on the day of irradiation (FIG. 2) or two days after irradiation (FIG. 3) substantially increased survival. Furthermore, AII administration at all time periods tested increased the number of circulating white blood cells (FIGS. 4–6). Further experiments demonstrated that AII administration increased the number of megakaryocytes (FIGS. 7–9), monocytes (FIGS. 10–12), neutrophils (FIGS. 13–15), and lymphocytes (FIGS. 16–18). These data demonstrate that in vivo administration of AII can improve hematopoietic recovery after irradiation.

EXAMPLE 2

Figure 20:
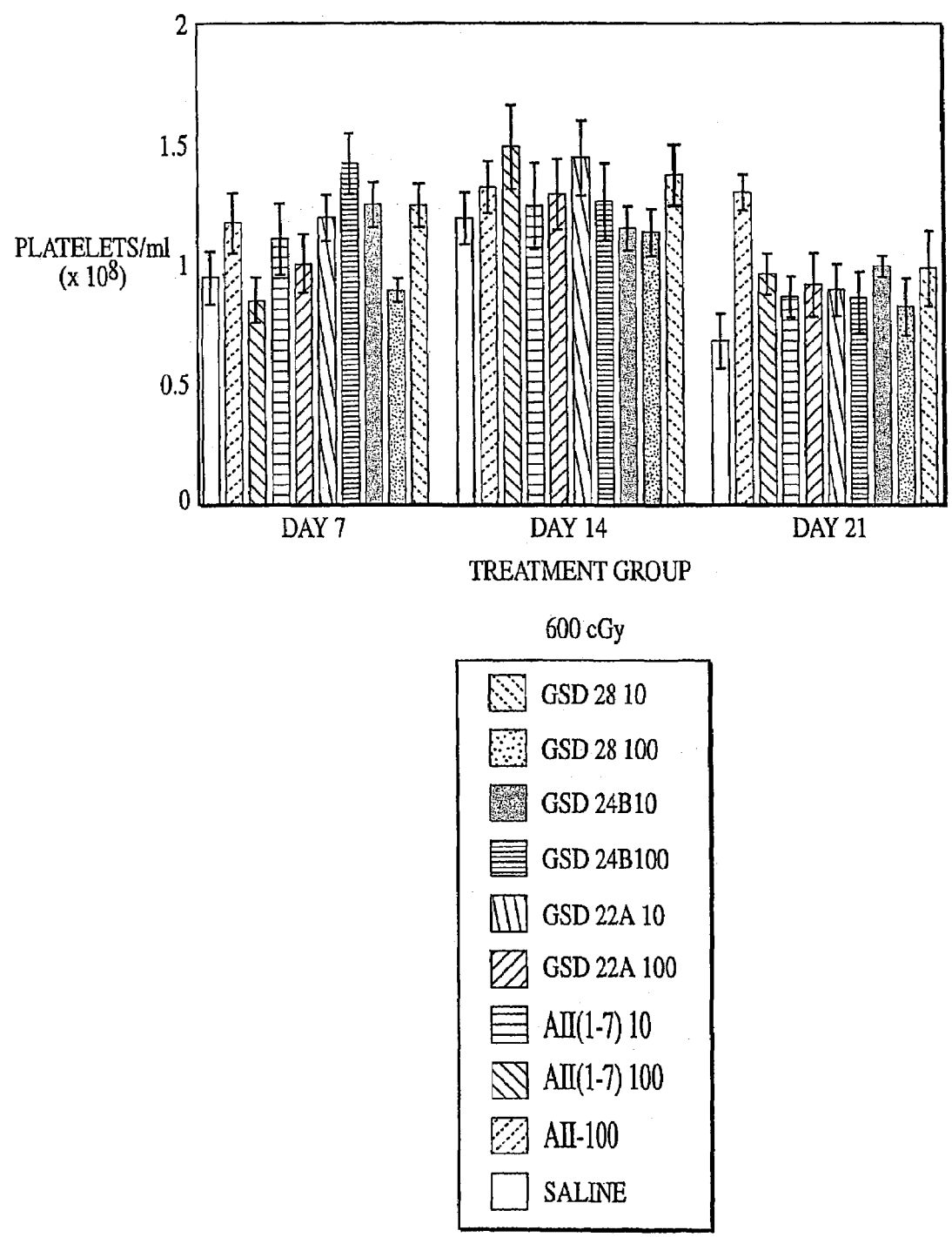
FIG. 20 is a graph showing is a graph showing the effect of AII analogues and fragments treatment on platelet number after irradiation.
Figure 21:
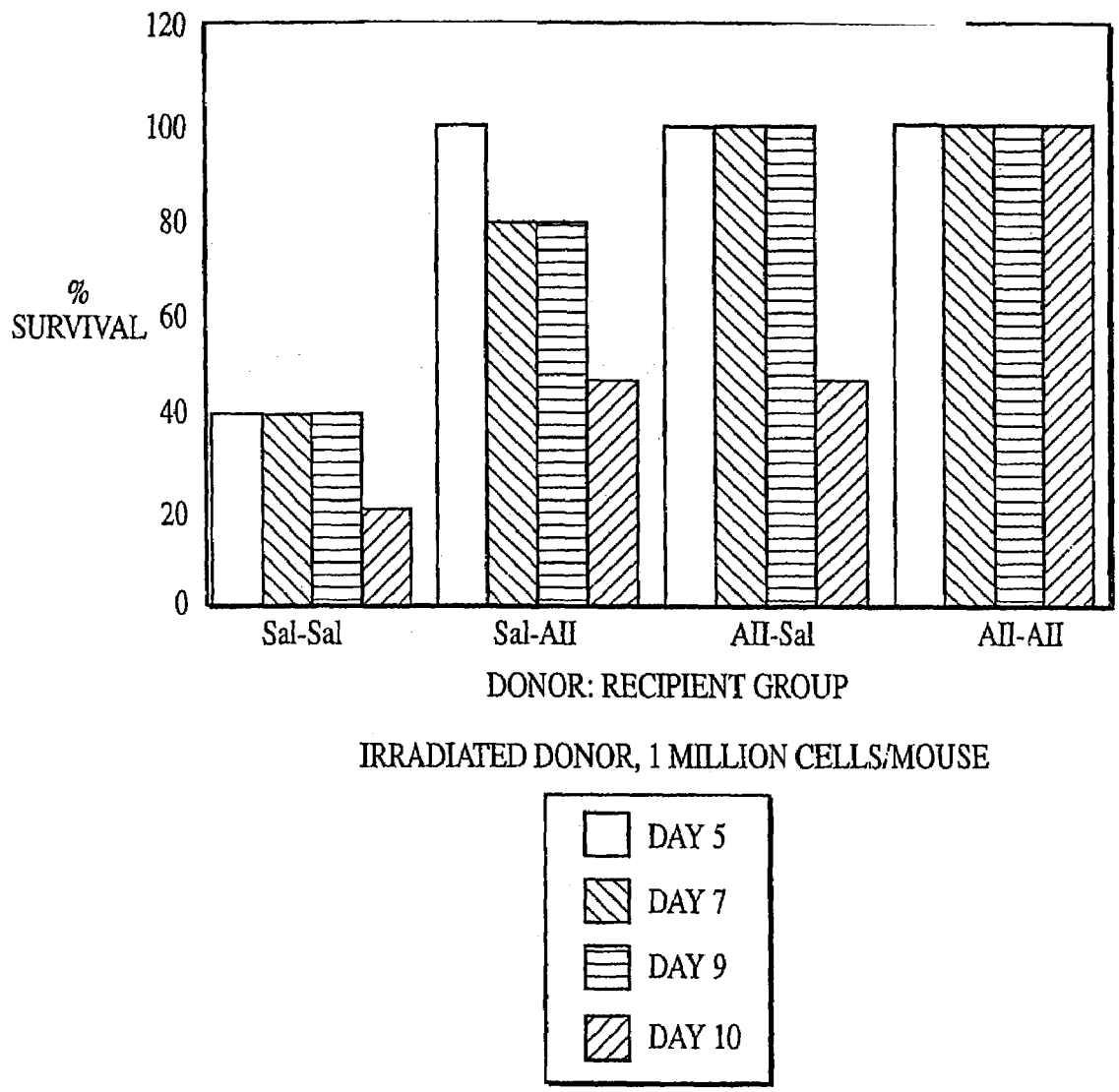
FIG. 21 is a graph showing the effect of AII on mouse survival receiving bone marrow transplantation after lethal irradiation.

Effect of AII and AII Analogs/Fragments on WBC and Platelet Numbers After Irradiation The animals were irradiated and treated as in Example 1, however, treatment started on day 0 only with one subcutaneous injection of either 10 μg/kg or 100 μg/kg daily until the study was terminated. Analogues and fragments of AII (see Table 3) were assessed for their effect on WBC recovery and platelet number after irradiation. The data are shown in FIGS. 20 and 21 and show that the peptides increase the production of both of these blood elements.

TABLE 3

Designation for Analogues/Fragments

| Name | Abbreviation | Sequence | SEQ ID NO: |
|---|---|---|---|
| GSD 28 | $Ile^8$-AII | DRVYIHPI | SEQ ID NO: 38 |
| GSD 24B | $Pro^3$-AII | DRPYIHPF | SEQ ID NO: 31 |
| GSD 22A | $Ala^4$-AIII | RVYAHPF | SEQ ID NO: 18 |
| AII(1–7) | | DRVYIHP | SEQ ID NO: 4 |
| AII | | DRVYIHPF | SEQ ID NO. 1 |

EXAMPLE 3

Effect of AII on Survival of Mice Receiving Bone Marrow Transplantation After Lethal Irradiation Donor C57B1/6 mice (female, 6–8 weeks old) were irradiated with 600 cGy total body irradiation. Starting on the day of irradiation, the mice received either saline (0.1 ml) or 20 μg/ml angiotensin II (0.1 ml, 100 μg/kg) subcutaneously for fourteen days. At the end of this period, the bone marrow was harvested from the femur by flushing and the number of viable nucleated cells determined by counting under a light microscope on a hemacytometer in the presence of trypan blue.

These donor bone marrow cells were then injected intravenously into recipient mice (female C57B1/6, 6–8 weeks old) that had been lethally irradiated (900 cGy total body irradiation) at two concentrations: $1\times10^6$ or $1\times10^5$ cells per mouse. After injection, the recipient mice received either saline or 100 μg/kg AII subcutaneously until death or termination. The study design in its entirety is as follows:

| Donor | Recipient | Cell Number |
|-------|-----------|-------------|
| Saline | Saline | $1 \times 10^6$ |
| Saline | Saline | $1 \times 10^5$ |
| Saline | AII | $1 \times 10^6$ |
| Saline | AII | $1 \times 10^5$ |
| AII | Saline | $1 \times 10^6$ |
| AII | Saline | $1 \times 10^5$ |
| AII | AII | $1 \times 10^6$ |
| AII | AII | $1 \times 10^5$ |

Figure 22:
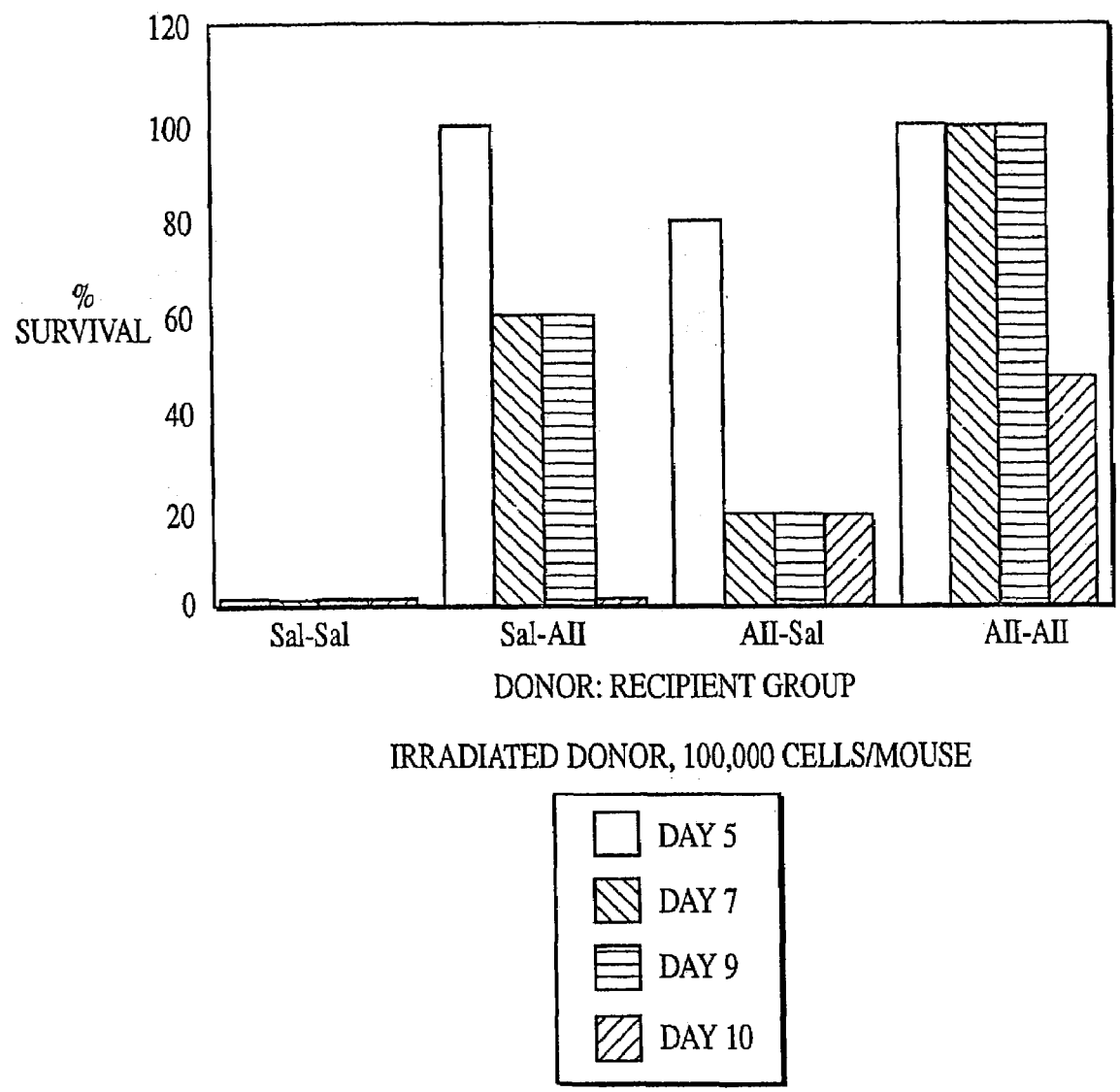
FIG. 22 is a graph showing the effect of AII analogues and fragments treatment on white blood cell number after irradiation.
Figure 23:
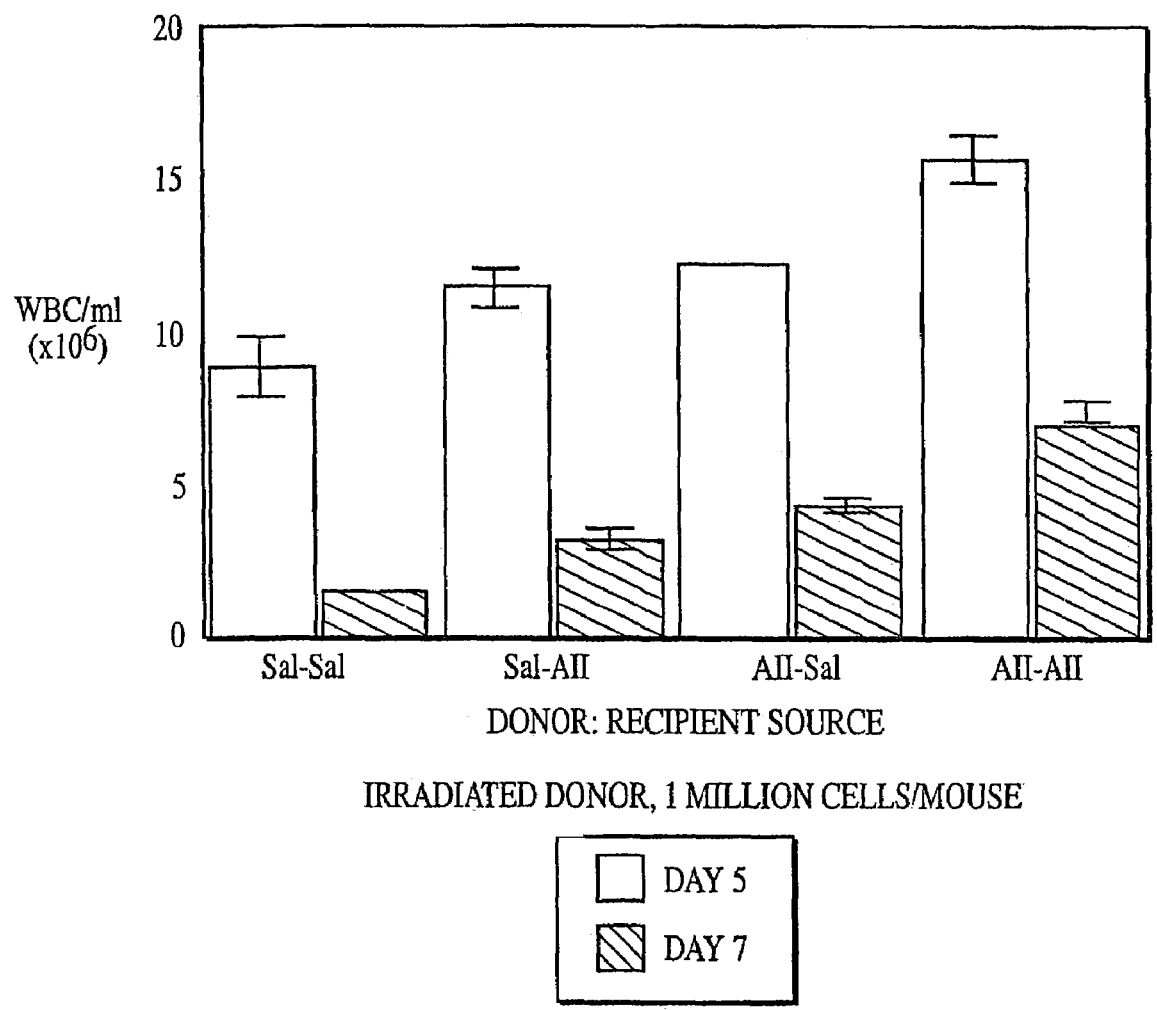
FIG. 23 is a graph showing the effect of AII on white blood cell number in the blood of mice receiving bone marrow transplantation after lethal irradiation.
Figure 24:
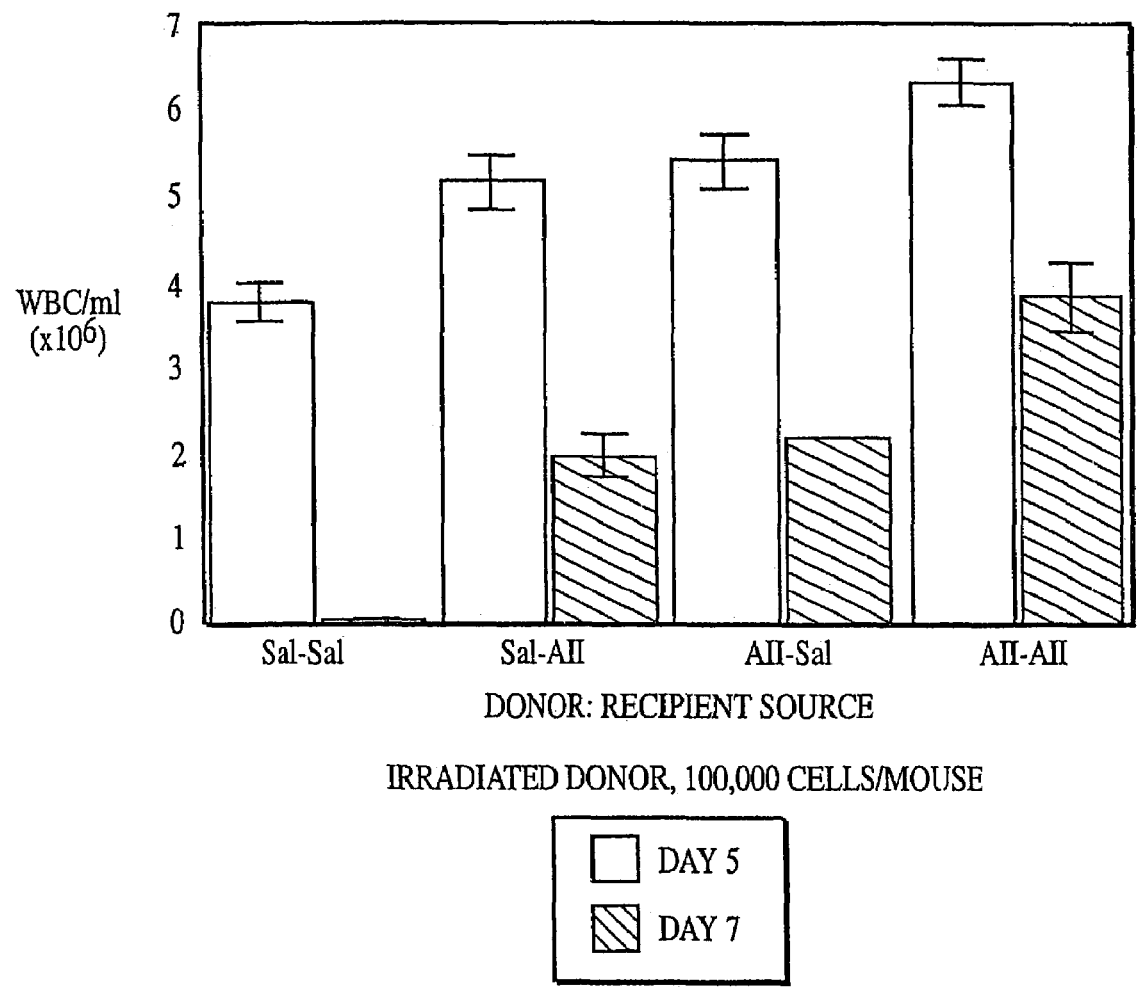
FIG. 24 is a graph showing the effect of AII on white blood cell number in the blood of mice receiving bone marrow transplantation after lethal irradiation.

The survival of the mice and the number of circulating white blood cells were measured as a function of time post-bone marrow transplantation. The data are presented in FIGS. 22–24, and demonstrate that AII treatment increased both survival and white blood cell number in mice receiving bone marrow transplantation after irradiation. The greatest benefit was conferred by treatment of both the donor bone marrow cells and the recipient mice with AII.

The methods and kits of the present invention, by mitigating radiation induced tissue damage and improving the efficacy of radiation therapy, significantly enhance the utility of presently available treatments both for radiation-induced tissue damage and for clinical radiation therapy, as well as bone marrow transplantation by increasing the survival rate of patients and accelerating the reconstitution of the patient's hematopoietic system. Similarly, by providing a method for megakaryocyte and platelet production, the present invention will greatly augment clinical cancer treatments and bone marrow transplantation and other conditions that lead to decreased megakaryocyte production and mobilization and platelet production.

The method of the present invention also increases the potential utility of megakaryocytes as vehicles for gene therapy in hematopoietic disorders, by providing a more efficient means to rapidly expand transfected megakaryocytes.

It is to be understood that the invention is not to be limited to the exact details of operation, or to the exact compounds, compositions, methods, procedures or embodiments shown and described, as obvious modifications and equivalents will be apparent to one skilled in the art, and the invention is therefore to be limited only by the full scope of the appended claims.

We claim:

1. A method for the mitigation of damage to cells selected from the group consisting of hematopoietic stem cells, hematopoietic progenitor cells, white blood cells, and platelets due to radiation exposure comprising the administration of an amount effective for the mitigation of damage to the cells of at least one composition comprising a polypeptide consisting of at least seven contiguous amino acids of groups $R^1$–$R^8$ in the sequence of general formula I $$R^1\text{-}R^2\text{-}R^3\text{-}R^4\text{-}R^5\text{-}R^6\text{-}R^7\text{-}R^8$$

wherein $R^1$ is Asp;
$R^2$ is Arg;
$R^3$ selected from the group consisting of Val and Pro;
$R^4$ is Tyr;
$R^5$ selected from the group consisting of Ile, and Ala;
$R^6$ is His;
$R^7$ is Pro; and
$R^8$ is Ile.

2. The method of claim 1 wherein the active agent is selected from the group consisting of SEQ ID NO:4 and SEQ ID NO:38.

3. The method of claim 1, wherein the method is used to mitigate damage to hematopoietic stem cells due to radiation exposure.

4. The method of claim 1, wherein the method is used to mitigate damage to hematopoietic progenitor cells due to radiation exposure.

5. The method of claim 1, wherein the method is used to mitigate damage to white blood cells due to radiation exposure.

6. The method of claim 1, wherein the method is used to mitigate damage to platelets due to radiation exposure.

7. The method of claim 1, wherein the radiation exposure comprises exposure due to clinical radiation therapy.

8. The method of claim 1, wherein the polypeptide is SEQ ID NO:4.

9. The method of claim 3, wherein the polypeptide is SEQ ID NO:4.

10. The method of claim 4, wherein the polypeptide is SEQ ID NO:4.

11. The method of claim 5, wherein the polypeptide is SEQ ID NO:4.

12. The method of claim 6, wherein the polypeptide is SEQ ID NO:4.

13. The method of claim 7, wherein the polypeptide is SEQ ID NO:4.

14. The method of claim 1 wherein the radiation exposure comprises accidental exposure.

15. The method of claim 14 wherein the polypeptide is SEQ ID NO:4.

* * * * *

SEQUENCE LISTING

<160> NUMBER OF SEQ ID NOS: 38

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:AII

<400> SEQUENCE: 1

Asp Arg Val Tyr Ile His Pro Phe
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:AII (2-8)

<400> SEQUENCE: 2

Arg Val Tyr Ile His Pro Phe
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:AII (3-8)

<400> SEQUENCE: 3

Val Tyr Ile His Pro Phe
 1               5

<210> SEQ ID NO 4
<211> LENGTH: 7
<212> TYPE: PRT
<213> ORGANISM: Artificial Sequence
<220> FEATURE:

-continued

<223> OTHER INFORMATION: Description of Artificial Sequence:AII (1-7)

<400> SEQUENCE: 4

Asp Arg Val Tyr Ile His Pro
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:AII (2-7)

<400> SEQUENCE: 5

Arg Val Tyr Ile His Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:AII (3-7)

<400> SEQUENCE: 6

Val Tyr Ile His Pro
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:AII (5-8)

<400> SEQUENCE: 7

Ile His Pro Phe
 1

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:AII (1-6)

<400> SEQUENCE: 8

Asp Arg Val Tyr Ile His
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:AII (1-5)

<400> SEQUENCE: 9

Asp Arg Val Tyr Ile
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:AII (1-4)

```
<400> SEQUENCE: 10

Asp Arg Val Tyr
 1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:AII (1-3)

<400> SEQUENCE: 11

Asp Arg Val
 1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (2)
<223> OTHER INFORMATION: Nle

<400> SEQUENCE: 12

Arg Xaa Tyr Ile His Pro Phe
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (4)
<223> OTHER INFORMATION: Nle

<400> SEQUENCE: 13

Arg Val Tyr Xaa His Pro Phe
 1               5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence:AII (6-8)

<400> SEQUENCE: 14

His Pro Phe
 1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:AII (4-8)

<400> SEQUENCE: 15

Tyr Ile His Pro Phe
 1               5
```

```
<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:AII analogue
      class
<220> FEATURE:
<221> NAME/KEY: UNSURE
<222> LOCATION: (1)
<223> OTHER INFORMATION: Xaa at poistion 1 can be Arg, Lys, Ala, Orn,
      Ser, MeGly, D-Arg, or D-Lys
<220> FEATURE:
<221> NAME/KEY: UNSURE
<222> LOCATION: (2)
<223> OTHER INFORMATION: Xaa at position 2 can be Val, Ala, Leu, Nle,
      Ile, Gly, Pro, Aib, Acp, or Tyr
<220> FEATURE:
<221> NAME/KEY: UNSURE
<222> LOCATION: (4)
<223> OTHER INFORMATION: Xaa at position 4 can be Ile, Ala, Leu, Nle,
      Val, or Gly

<400> SEQUENCE: 16

Xaa Xaa Tyr Xaa His Pro Phe
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 17

Arg Val Tyr Gly His Pro Phe
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 18

Arg Val Tyr Ala His Pro Phe
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:AII
      analogue 1

<400> SEQUENCE: 19

Asp Arg Val Tyr Val His Pro Phe
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:AII
      analogue 2

<400> SEQUENCE: 20
```

Asn Arg Val Tyr Val His Pro Phe
 1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence:AII
      analogue 3

<400> SEQUENCE: 21

Ala Pro Gly Asp Arg Ile Tyr Val His Pro Phe
 1               5                  10

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:AII
      analogue 4

<400> SEQUENCE: 22

Glu Arg Val Tyr Ile His Pro Phe
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:AII
      analogue 5

<400> SEQUENCE: 23

Asp Lys Val Tyr Ile His Pro Phe
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:AII
      analogue 6

<400> SEQUENCE: 24

Asp Arg Ala Tyr Ile His Pro Phe
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:AII
      analogue 7

<400> SEQUENCE: 25

Asp Arg Val Thr Ile His Pro Phe
 1               5

<210> SEQ ID NO 26
<211> LENGTH: 8
<212> TYPE: PRT
<213> ORGANISM: Artificial Sequence

```
<220> FEATURE:
<223> OTHER INFORMATION: Description of Artificial Sequence:AII
      analogue 8

<400> SEQUENCE: 26

Asp Arg Val Tyr Leu His Pro Phe
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:AII
      analogue 9

<400> SEQUENCE: 27

Asp Arg Val Tyr Ile Arg Pro Phe
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:AII
      analogue 10

<400> SEQUENCE: 28

Asp Arg Val Tyr Ile His Ala Phe
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:AII
      analogue 11

<400> SEQUENCE: 29

Asp Arg Val Tyr Ile His Pro Tyr
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:AII
      analogue 12

<400> SEQUENCE: 30

Pro Arg Val Tyr Ile His Pro Phe
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:AII
      analogue 13

<400> SEQUENCE: 31

Asp Arg Pro Tyr Ile His Pro Phe
 1               5
```

```
<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:AII
      analogue 14
<220> FEATURE:
<221> NAME/KEY: MOD_RES
<222> LOCATION: (4)
<223> OTHER INFORMATION: PHOSPHORYLATION

<400> SEQUENCE: 32

Asp Arg Val Tyr Ile His Pro Phe
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:AII
      analogue 15
<220> FEATURE:
<221> NAME/KEY: MOD_RES
<222> LOCATION: (3)
<223> OTHER INFORMATION: Nle

<400> SEQUENCE: 33

Asp Arg Xaa Tyr Ile His Pro Phe
 1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:AII
      analogue 16
<220> FEATURE:
<221> NAME/KEY: MOD_RES
<222> LOCATION: (5)
<223> OTHER INFORMATION: Nle

<400> SEQUENCE: 34

Asp Arg Val Tyr Xaa His Pro Phe
 1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:AII
      analogue 17
<220> FEATURE:
<221> NAME/KEY: MOD_RES
<222> LOCATION: (4)
<223> OTHER INFORMATION: homo Ser

<400> SEQUENCE: 35

Asp Arg Val Ser Tyr Ile His Pro Phe
 1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial
```

```
        Sequence:p-aminophenylalanine 6 AII
<220> FEATURE:
<221> NAME/KEY: MOD_RES
<222> LOCATION: (6)
<223> OTHER INFORMATION: p-aminophenylalanine

<400> SEQUENCE: 36

Asp Arg Val Tyr Ile Xaa Pro Phe
 1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence:
      angiotensin I

<400> SEQUENCE: 37

Asp Arg Val Tyr Ile His Pro Phe His Leu
 1               5                  10

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence:1GD:
      Ile8-AII

<400> SEQUENCE: 38

Asp Arg Val Tyr Ile His Pro Ile
 1               5
```